(12) United States Patent
Tabuchi et al.

(10) Patent No.: US 9,238,687 B2
(45) Date of Patent: *Jan. 19, 2016

(54) METHOD FOR RECOMBINANT PRODUCTION OF A DESIRED POLYPEPTIDE USING A MAMMALIAN CELL CO-EXPRESSING A TAURINE TRANSPORTER POLYPEPTIDE

(75) Inventors: Hisahiro Tabuchi, Tokyo (JP); Tomoya Sugiyama, Tokyo (JP); Saeko Tanaka, Tokyo (JP); Satoshi Tainaka, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/226,195

(22) PCT Filed: Apr. 12, 2007

(86) PCT No.: PCT/JP2007/058049
§ 371 (c)(1),
(2), (4) Date: Oct. 10, 2008

(87) PCT Pub. No.: WO2007/119774
PCT Pub. Date: Oct. 25, 2007

(65) Prior Publication Data
US 2009/0191591 A1   Jul. 30, 2009

(30) Foreign Application Priority Data
Apr. 13, 2006   (JP) ................. 2006-110467

(51) Int. Cl.
| | |
|---|---|
| C12P 21/06 | (2006.01) |
| C07H 21/04 | (2006.01) |
| C12N 15/00 | (2006.01) |
| C12N 5/07 | (2010.01) |
| C12N 1/20 | (2006.01) |
| C07K 14/705 | (2006.01) |
| C12P 21/02 | (2006.01) |

(52) U.S. Cl.
CPC ............. *C07K 14/705* (2013.01); *C12P 21/02* (2013.01); *C12N 2500/33* (2013.01); *C12N 2510/02* (2013.01)

(58) Field of Classification Search
None
See application file for complete search history.

(56) References Cited

U.S. PATENT DOCUMENTS

| | | |
|---|---|---|
| 5,658,786 A | 8/1997 | Smith et al. |
| 6,184,007 B1 | 2/2001 | Dusch et al. |
| 6,225,115 B1 | 5/2001 | Smith et al. |
| 6,251,613 B1 | 6/2001 | Kishimoto et al. |
| 6,316,238 B1 | 11/2001 | Nakamura et al. |
| 6,812,339 B1 | 11/2004 | Venter et al. |
| 7,413,536 B1 | 8/2008 | Dower et al. |
| 7,919,086 B2 | 4/2011 | Nakano et al. |
| 8,697,397 B2 * | 4/2014 | Tabuchi et al. ............. 435/70.3 |
| 2003/0064510 A1 * | 4/2003 | Reff et al. ................. 435/325 |
| 2003/0165495 A1 | 9/2003 | Carulli et al. |
| 2005/0221466 A1 | 10/2005 | Liao et al. |
| 2005/0265983 A1 | 12/2005 | Melamed et al. |
| 2006/0014937 A1 * | 1/2006 | Kang et al. ................. 530/387.3 |
| 2007/0162995 A1 | 7/2007 | Good et al. |
| 2007/0166362 A1 | 7/2007 | Sakuma et al. |
| 2007/0190599 A1 | 8/2007 | Nakano et al. |
| 2009/0221442 A1 | 9/2009 | Dower et al. |
| 2010/0167346 A1 | 7/2010 | Tabuchi et al. |
| 2010/0233759 A1 | 9/2010 | Tabuchi et al. |
| 2010/0248359 A1 | 9/2010 | Nakano et al. |
| 2011/0003334 A1 | 1/2011 | Tabuchi et al. |
| 2011/0014654 A1 | 1/2011 | Tabuchi et al. |
| 2012/0045795 A1 | 2/2012 | Tabuchi et al. |

FOREIGN PATENT DOCUMENTS

| | | |
|---|---|---|
| CN | 1612689 A | 5/2005 |
| CN | 1838969 A | 9/2006 |
| EP | 1 212 619 B1 | 5/2007 |
| EP | 2 213 746 A1 | 8/2010 |
| JP | 08-191693 A | 7/1996 |
| JP | 10-075787 A | 3/1998 |
| JP | 10-191984 A | 7/1998 |
| JP | 2000-228990 A | 8/2000 |
| JP | 2005-525100 A | 8/2005 |
| JP | 2006-506086 A | 2/2006 |
| WO | WO-92/04381 A1 | 3/1992 |
| WO | WO-97/27485 A1 | 7/1997 |
| WO | WO-01/20331 A1 | 3/2001 |
| WO | WO-02/092768 A2 | 11/2002 |
| WO | WO-03/039485 A2 | 5/2003 |
| WO | WO 2005/076015 A1 | 8/2005 |
| WO | WO-2006/006693 A1 | 1/2006 |

(Continued)

OTHER PUBLICATIONS

Tinland et al., PNAS 91:8000-8004, 1994.*
Ramamoorthy et al., Biochem. J. 300:893-900, 1994.*
Kim et al., J. Biotechnol. 95:237-248, 2002.*
Ito et al., Biochem. J. 382:177-182, 2004.*
Han et al., "Mechanisms of Regulation of Taurine Transporter Activity", Taurine 6, Edited by Oja and Saransaari, Springer, New York 2006, pp. 79-90.*
Liu et al., "Cloning and expression of a cDNA encoding the transporter of taurine and β-alanine in mouse brain," Proc. Natl. Acad. Sci. USA, Dec. 1992, 89(24):12145-12149.

(Continued)

Primary Examiner — David J Steadman
(74) Attorney, Agent, or Firm — Foley & Lardner LLP

(57) ABSTRACT

The present invention provides a method capable of producing a natural or recombinant protein at low cost. The present invention relates to a method of producing a polypeptide, comprising culturing a cell which strongly expresses a taurine transporter and has a transferred DNA encoding a desired polypeptide and thereby allowing the cell to produce the polypeptide. Hamster taurine transporter, a DNA encoding the same, a recombinant vector and a transformed cell are also provided.

8 Claims, 10 Drawing Sheets

(56) References Cited

FOREIGN PATENT DOCUMENTS

| WO | WO-2006/119115 A2 | 11/2006 |
| WO | WO-2007/056507 A1 | 5/2007 |
| WO | WO-2007/119774 A1 | 10/2007 |
| WO | WO-2008/114673 A1 | 9/2008 |
| WO | WO-2009/020144 A1 | 2/2009 |
| WO | WO-2009/051109 A1 | 4/2009 |
| WO | WO-2009/054433 A1 | 4/2009 |

OTHER PUBLICATIONS

Smith et al., "Cloning and Expression of a High Affinity Taurine Transporter from Rat Brain," Mol. Pharmacol., 1992, 42(4):563-569.
Supplementary European Search Report and European Search Opinion dated Oct. 9, 2009, in corresponding EP 07741485.2, 12 pages.
Ganapathy et al., "Expression and Regulation of the Taurine Transporter in Cultured Cell Lines of Human Origin," Advances in Experimental Medicine and Biology, 1994, 359:51-57, XP009123192.
Jhiang et al., "Cloning of the human taurine transporter and characterization of taurine uptake in thyroid cells," FEBS Letters, Mar. 1, 1993, 318(2):139-144.
Uchida et al., "Molecular cloning of the cDNA for an MDCK cell $Na^+$- and $Cl^-$-dependent taurine transporter that is regulated by hypertonicity," Proc. Natl. Acad. Sci. USA, Sep. 1992, 89:8230-8234.
Voss et al., "Regulation of the expression and subcellular localization of the taurine transporter TauT in mouse NIH3T3 fibroblasts," Eur. J. Biochem., 2004, 271:4646-4658.
European Search Report dated Aug. 5, 2010 in corresponding EP 10157011.7, 11 pages.
Database UniProt [Online] Jul. 1, 1993, XP002493028, retrieved from EBI accession No. UNIPROT:Q00589, 2 pages.
Database EMBL [Online] Jul. 23, 1992, XP002593029, retrieved from EBI accession No. EMBL:M95495, 3 pages.
Database Uniprot [Online] Oct. 1, 2000, XP002593031, retrieved from EBI accession No. UNIPROT:Q9MZ34, 2 pages.
Database Uniprot [Online] Mar. 15, 2005, XP002593030, retrieved from EBI accession No. UNIPROT:Q5F431, 1 page.
Database Uniprot [Online] Jan. 10, 2006, XP002593032, retrieved from EBI accession No. UNIPROT:Q2VRP7, 1 page.
Jhiang et al., "Cloning of the human taurine transporter and characterization of taurine uptake in thyroid cells," FEBS Letters, Mar. 1993, 318(2):139-144.
Liu et al., "Cloning and expression of a cDNA encoding the transporter of taurine and β-alanine in mouse brain," PNAS, Dec. 1992, 89(24):12145-12149.
Miyasaka et al., "Characterization of Human Taurine Transporter Expressed in Insect Cells Using a Recombinant Baculovirus," Protein Expression and Purification, 2001, 23(3):389-397.
Smith et al., "Cloning and Expression of a High Affinity Taurine Transporter from Rat Brain," Molecular Pharmacology, 1992, 42(4):563-569.
Uchida et al., "Molecular cloning of the cDNA for an MDCK cell $Na^+$- and $CL^-$-dependent taurine transporter that is regulated by hypertonicity," PNAS, Sep. 1992, 89(17):8230-8234.
Voss et al., "Regulation of the expression and subcellular localization of the taurine transporter TauT in mouse NIH3T3 fibroblasts," Eur. J. Biochem., Dec. 2004, 271(23-24):4646-4658.
Office Action dated Jul. 8, 2010, in corresponding EP 07 741 485.2, 4 pages.
Butler, Michael, "Animal cell cultures: recent achievements and perspectives in the production of biopharmaceuticals," Appl. Microbiol. Biotechnol., 2005, 68:283-291.
Trill et al., "Production of monoclonal antibodies in COS and CHO cells," Current Opinion in Biotechnology, 1995, 6:553-560.
Beckmann et al., "Coexpression of band 3 mutants and Rh polypeptides: differential effects of band 3 on the expression of the Rh complex containing D polypeptide and the Rh complex containing CcEe polypeptide," Blood, Apr. 15, 2001, 97(8):2496-2505.
Han et al., "Regulation of TauT by cisplatin in LLC-PK1 renal cells," Pediatr. Nephrol., 2005, 20:1067-1072.
Ishiguro et al., "CO2 permeability and bicarbonate transport in microperfused interlobular ducts isolated from guinea-pig pancreas," Journal of Physiology, 2000, 528.2:305-315.
Mount et al., "The SLC26 gene family of multifunctional anion exchangers," Pflugers Arch.—Eur. J. Physiol., 2004, 447:710-721.
Pushkin et al., "SLC4 base (HCO-3, CO-23) transporters: classification, function, structure, genetic diseases, and knockout models," Am. J. Physiol. Renal Physiol., 2006, 290:F580-F599.
Final Office Action dated Mar. 2, 2012 in U.S. Appl. No. 12/734,283.
Final Office Action dated Aug. 23, 2011 in U.S. Appl. No. 12/733,815.
Notice of Allowance dated Dec. 20, 2012 in U.S. Appl. No. 12/733,052.
Office Action dated Jan. 6, 2011 in U.S. Appl. No. 12/733,815.
Office Action dated Aug. 3, 2011 in U.S. Appl. No. 12/734,283.
Office Action dated Sep. 21, 2012 in U.S. Appl. No. 13/368,945.
Shibayama et al., "Effect of Methotrexate Treatment on Expression Levels of Organic Anion Transporter Polypeptide 2,P-Glycoprotein and Bile Salt Export Pump in Rats," Biol. Pharm. Bull., Mar. 2009, 32(3):493-496.
Office Action dated Feb. 27, 2013 in U.S. Appl. No. 13/138,909.
Final Office Action dated May 24, 2013 in U.S. Appl. No. 13/368,945.
Tanner et al., "The complete amino acid sequence of the human erythrocyte membrane anion-transport protein deduced from the cDNA sequence," Biochem. J., 1988, 256:703-712.
U.S. Appl. No. 13/368,945, filed Feb. 8, 2012, Tabuchi et al.
Alper, Seth L., "Molecular physiology of SLC4 anion exchangers," Exp. Physiol., 2006, 91:153-161.
Arden et al., "Life and death in mammalian cell culture: strategies for apoptosis inhibition," Trends in Biotechnology, Apr. 2004, 22(4):174-180.
Bell et al., "Genetic Engineering of Hybridoma Glutamine Metabolism," Enzyme and Microbial Technology, 1995, 17(2):98-106.
Butler, Michael, "Animal cell cultures: recent achievements and perspectives in the production of biopharmaceuticals," Appl. Microbiol. Biotechnol., Aug. 2005, 68(3):283-291.
Chambard et al., "Sugar transport by mammalian members of the SLC26 superfamily of anion-bicarbonate exchangers," J. Physiol., 2003, 550:667-677.
Christensen et al., "High expression of the taurine transporter TauT in primary cilia of NIH3T3 fibroblasts," Cell Biology International, 2005, 29:347-351.
Christie et al., "The Adaptation of BHK Cells to a Non-Ammoniagenic Glutamate-Based Culture Medium," Biotechnology and Bioengineering, Aug. 5, 1999, 64(3):298-309.
Database DDBJ/EMBL/GenBank [online], Accession No. NM_000342, uploaded Sep. 25, 2007, Keskanokwong et al., Definition: Homo sapiens solute carrier family 4, anion exchanger, member 1 (erythrocyte membrane protein band 3, Diego blood group) (SLC4A1), mRNA, retrieved Nov. 11, 2008, 12 pages.
Database UniProt [Online] Jun. 1, 2001, "RecName: Full=Cysteine sulfinic acid decarboxylase; EC=4.1.1.29; AltName: Full=Cysteinesulfinate decarboxylase; AltName: Full=Sulfinoalanine decarboxylase;" XP002597738 retrieved from EBI accession No. UNIPROT:Q9DBE0 Database accession No. Q9DBE0, 2 pages.
de la Cruz Edmonds et al., "Development of Transfection and High-Producer Screening Protocols for the CHOK1SV Cell System," Molecular Biology, Oct. 1, 2006, 34(2):179-190.
de la Rosa et al., "Evidence for a Rate-Limiting Role of Cysteinesulfinate Decarboxylase Activity in Taurine Biosynthesis In Vivo," Comp. Biochem. Physiol., 1985, 81B(3):565-571.
Dusch et al., "Expression of the Corynebacterium glutamicum panD Gene Encoding L-Aspartate-alpha-Decarboxylase Leads to Pantothenate Overproduction in Escherichia coli," Applied and Environmental Microbiology, Apr. 1999, 65(4):1530-1539.
Final Office Action dated Mar. 1, 2012 in U.S. Appl. No. 12/733,052.
Fu et al., "Direct interaction and cooperative role of tumor suppressor p16 with band 3 (AE1)," FEBS Letters, 2005, 579(10):2105-2110.
GenBank Accession No. AEQ38544, Oct. 2011, 2 pages.
GenBank Accession No. EGW01898, Aug. 2011, 2 pages.

(56) References Cited

OTHER PUBLICATIONS

Good et al., "Engineering nitrogen use efficiency with alanine aminotransferase," Canadian Journal of Botany, Mar. 1, 2007, 85(3):252-262.

Griffith, Owen W., "Crysteinesulfinate Metabolism, Altered Partitioning Between Transamination and Decarboxylation Following Administration of β-Methyleneaspartate," J. Biol. Chem., Feb. 10, 1983, 258(3):1591-1598.

Hammer et al., "β-Alanine but not taurine can function as an organic osmolyte in preimplantation mouse embryos cultured from fertilized eggs," Molecular Reproduction and Development, Oct. 2003, 66(2):153-161.

Han et al., "Is TauT an Anti-Apoptotic Gene?" Taurine 6, Oja et al. Eds., 2006, 59-67.

Hwang et al., "Expression and purification of recombinant human angiopoietin-2 produced in Chinese hamster ovary cells," Protein Expression and Purification, 2005, 39:175-183.

Ifandi et al., "Regulation of Cell Proliferation and Apoptosis in CHO-K1 Cells by the Coexpression of c-Myc and Bcl-2," Biotechnol. Prog., 2005, 21:671-677.

Jhiang et al., "Cloning of the human taurine transporter and characterization of taurine uptake in thyroid cells," FEBS, 318(2):139-144, 1993.

Kalwy et al., "Toward More Efficient Protein Expression," Molecular Biotechnology, Oct. 2006, 34(2):151-156.

Kennel et al,. "Principles and Practices of Nucleic Acid Hybridization," Prog. Nucleic Acid Res. Mol. Biol., 1971, 11:259-270.

Kim et al., "Characterization of Chimeric Antibody Producing CHO Cells in the Course of Dihydrofolate Reductase-Mediated Gene Amplification and Their Stability in the Absence of Selective Pressure," Biotechnology and Bioengineering, Apr. 5, 1998, 58(1):73-84.

Kondo et al., "Modulation of apoptosis by endogenous Bcl-xL expression in MKN-45 human gastric cancer cells," Oncogene, 1998, 17:2585-2591.

Lee et al., "Development of Apoptosis-Resistant Dihydrofolate Reductase-Deficient Chinese Hamster Ovary Cell Line," Biotechnol. Bioengineer., 2003, 82:872-876.

Liu et al., "Cloning and expression of a cDNA encoding the transporter taurine and β-alanine in mouse brain," Proc. Natl. Acad. Sci. USA, Dec. 1992, 89:12145-12149.

Lux et al., "Cloning and characterization of band 3, the human erythrocyte anion-exchange protein (AE1)," Proc. Natl. Acad. Sci. USA, Dec. 1989, 86:9089-9093.

Miyasaka et al., "Characterization of Human Taurine Transporter Expressed in Insect Cells Using a Recombinant Baculovirus," Protein Expression and Purification, 2001, 23:389-397.

Morgan et al., "Interactions of transmembrane carbonic anhydrase, CAIX, with bicarbonate transporters," Am. J. Physiol. Cell Physiol., Aug. 2007, 293(2):C738-C748.

Ngo et al., "Computational Complexity, Protein Structure Prediction, and the Levinthal Paradox," The Protein Folding Problem and Tertiary Structure Prediction, Merz et al. (Eds.), 1994, 433 and 492-495.

Office Action dated May 12, 2011 in U.S. Appl. No. 12/733,052.

Office Action dated Aug. 9, 2011 in U.S. Appl. No. 12/450,161.

Porter et al., "Non-steady-state kinetics of brain glutamate decarboxylase resulting from interconversion of the apo- and holoenzyme," Biochimica et Biophysica Acta, 1988, 874:235-244.

Reymond et al., "Molecular cloning and sequence analysis of the cDNA encoding rat liver cysteine sulfinate decarboxylase (CSD)," Biochimica et Biophysica Acta, 1996, 1307:152-156.

Rudinger, J., "Characteristics of the amino acids as components of a peptide hormone sequence," Peptide Hormones, Parsons (Ed.), 1976, 1-7.

Shen et al., "Expression of Anion Exchanger 1 Sequestrates p16 in the Cytoplasm in Gastric and Colonic Adenocarcinoma," Neoplasia, Oct. 2007, 9(10):812-819.

Smith et al., "Cloning and Expression of a High Affinity Taurine Transporter from Rat Brain," Molecular Pharmacology, 1992, 42:563-569.

Tabuchi et al., "Overexpression of Taurine Transporter in Chinese Hamster Ovary cells Can Enhance Cell Viability and Product Yield, While Promoting Glutamine Consumption," Biotechnology and Bioengineering, 2010, 107(6):998-1003.

Tang et al., "Protein Phosphorylation and Taurine Biosynthesis In Vivo and In Vitro," Journal of Neuroscience, Sep. 15, 1997, 17(18):6947-6951.

Tappaz et al., "Characterization of the cDNA Coding for Rat Brain Cysteine Sulfinate Decarboxylase: Brain and Liver Enzymes are Identical Proteins Encoded by Two Distince mRNAs," J. Neurochem., 1999, 73(3):903-912.

Wirth et al., "Isolation of overproducing recombinant mammalian cell lines by a fast and simple selection procedure," Gene, 1988, 73:419-426.

Wu et al., "Overexpression of Anion Exchanger 2 in Human Hepatocellular Carcinoma," Chinese Journal of Physiology, 2006, 49(4):192-198.

Yang et al., "Human Hepatitis B Viral e Antigen Interacts with Cellular Interleukin-1 Receptor Accessory Protein and Triggers Interleukin-1 Response," Journal of Biological Chemistry, Nov. 10, 2006, 281(45):34525-34536.

Yang et al., "cDNA Cloning, Genomic Structure, Chromosomal Mapping, and Functional Expression of a Novel Human Alanine Aminotransferase," Genomics, Mar. 1, 2002, 79(3):445-450.

Zhang et al., "Metabolic characteristics of recombinant Chinese hamster ovary cells expressing glutamine synthetase in presence and absence of glutamine," Cytotechnology, 2006, 51(1):21-28.

Herman et al., "Low dose methotrexate induces apoptosis with reactive oxygen species involvement in T lymphocytic cell lines to a greater extent than in monocytic lines," Inflammation Research, 2005, 54:273-280.

\* cited by examiner

Fig. 1

Mean Viable Cell Density
( n=7 )

pHyg/TauT
( 9.28±3.27 )
x $10^5$ cells/ml
pHyg
( 5.69±2.09 )
x $10^5$ cells/ml t Test  P <0.05

Mean Lactate Concentration
( n=7 )

pHyg/TauT
( 1.54±0.20 ) g/L pHyg
( 1.75±0.15 ) g/L t Test  P <0.05

Mean Antibody Yield (n=7)

pHyg/TauT (397±69) mg/L pHyg (342±55) mg/L

Mean Antibody Yield (n=7)

pHyg/TauT (761±59) mg/L pHyg (662±56) mg/L t Test P <0.01

SEQUENCE LISTING

<160> NUMBER OF SEQ ID NOS: 8

<210> SEQ ID NO 1
<211> LENGTH: 1869
<212> TYPE: DNA
<213> ORGANISM: Cricetulus griseus

<400> SEQUENCE: 1

```
atggccacca aggagaagct gcagtgtctg aaagacttcc acaagacat cctgaagcct      60 tctccaggga agagcccagg cacacggcct gaggatgagg ctgaggggaa gccccctcag     120
agggagaagt ggtccagcaa gattgacttt gtgctgtctg tggccggagg cttcgtgggt     180
ttgggcaacg tttggcgttt cccgtacctc tgctacaaaa atggtggagg tgctttcctc     240
ataccgtatt ttatttcct gtttgggagt ggcctgcctg tgttttcct ggaggtcata      300 ataggccagt acacctcaga aggggaatc acctgctggg agaagatctg cccttgttc      360 tctggcattg gctacgcatc catcgtcatc gtgtccctcc tgaatgtgta ctacattgtc     420
atcctggcct gggccacata ctacctattt cactccttcc agacagagct tccctgggcc     480
cactgcaacc acagctggaa cacaccacat tgcatggagg acaccctgcg taggaatgag     540
agtctctggg tctcccttag cgcctccaac ttcacctcgc ctgtcatcga gttctgggag     600
cgcaatgtac tcagcctgtc ttccggaatc gacgaaccag gcgctctgaa atgggaccttt    660 gcgctctgcc tcctcttagt ctggcttgtc tgtttttcct gcatatggaa gggtgttcga     720
tccacaggca aggttgtcta cttcaccgcc actttcccgt ttgccatgct tctggtgctg     780
ctggtccgtg gactgaccct gccgggtgct ggcgaaggca tcaaattcta cctgtaccct    840
gacatcagcc gccttgagga cccacaggtg tggatcgacg ccggaacccca gatattcttt    900 tcctatgcca tctgcctggg ggccatgacc tcactgggaa gctacaacaa gtacaagtat     960
aactcgtaca gggactgtat gctgctggga tgcctgaaca gtggtaccag ttttgtgtct    1020
ggcttcgcag ttttttccat cctgggcttc atggcacaag agcaaggggt ggacattgct    1080
gatgtggctg agtcaggtcc tggcttggcc ttcattgcct atccaaaagc tgtgactatg    1140
atgccgctgc ccacctttg gtccattctg ttttttatta tgctcctctt gcttggactg    1200
gacagccagt tgttgaagt cgaaggacag atcacatcct tggttgatct ttaccgtcc    1260 ttcctaagga agggtatcg tcgggaagtc ttcatcgcca tcctgtgtag catcagctac   1320
ctgctggggc tgtcgatggt gacgagggt ggcatgtatg tgtttcaact ctttgactac   1380
tatgcagcta gtggtgtatg ccttttgtgg gttgcattct ttgaatgttt tgttattgcc   1440
tggatatatg gtgtgataa cttatatgac ggtattgagg acatgattgg ctatcggcct   1500
gggccctgga tgaagtacag ctgggctgtc atcactccag ttctctgtgc tggatgtttc   1560
atcttctctc ttgtcaagta tgtaccctg acctacaaca agtctacgt gtatcctgat   1620 tgggcaattg ggctgggctg gggcctggcc ctatcctcca tggtgtgtat cccttggtc    1680 attgccatcc tcctctgccg gacggaggga ccgttccgcg tgagaatcca ataccggata   1740
```

-continued

```
acccccaggg agcccaaccg ctgggctgtg gagcgtgagg gggccacacc cttccactcc    1800
cgcacaagcc tcgtcatgaa cggcgcactc atgaaaccca gtcacgtcat tgtggagacc    1860
atgatgtga                                                             1869
```

<210> SEQ ID NO 2
<211> LENGTH: 622
<212> TYPE: PRT
<213> ORGANISM: Cricetulus griseus

<400> SEQUENCE: 2

```
Met Ala Thr Lys Glu Lys Leu Gln Cys Leu Lys Asp Phe His Lys Asp
  1               5                  10                  15

Ile Leu Lys Pro Ser Pro Gly Lys Ser Pro Gly Thr Arg Pro Glu Asp
             20                  25                  30

Glu Ala Glu Gly Lys Pro Pro Gln Arg Glu Lys Trp Ser Ser Lys Ile
         35                  40                  45

Asp Phe Val Leu Ser Val Ala Gly Gly Phe Val Gly Leu Gly Asn Val
     50                  55                  60

Trp Arg Phe Pro Tyr Leu Cys Tyr Lys Asn Gly Gly Gly Ala Phe Leu
 65                  70                  75                  80

Ile Pro Tyr Phe Ile Phe Leu Phe Gly Ser Gly Leu Pro Val Phe Phe
                 85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp
    130                 135                 140

Ala Thr Tyr Tyr Leu Phe His Ser Phe Gln Thr Glu Leu Pro Trp Ala
145                 150                 155                 160

His Cys Asn His Ser Trp Asn Thr Pro His Cys Met Glu Asp Thr Leu
                165                 170                 175

Arg Arg Asn Glu Ser Leu Trp Val Ser Leu Ser Ala Ser Asn Phe Thr
            180                 185                 190

Ser Pro Val Ile Glu Phe Trp Glu Arg Asn Val Leu Ser Leu Ser Ser
        195                 200                 205

Gly Ile Asp Glu Pro Gly Ala Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asp Ile Ser Arg Leu Glu Asp Pro
        275                 280                 285

Gln Val Trp Ile Asp Ala Gly Thr Gln Ile Phe Phe Ser Tyr Ala Ile
    290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Val Phe Ser Ile Leu Gly Phe Met Ala
```

|   |   |   | 340 |   |   |   | 345 |   |   |   | 350 |   |
|---|---|---|---|---|---|---|---|---|---|---|---|---|

Gln Glu Gln Gly Val Asp Ile Ala Asp Val Ala Glu Ser Gly Pro Gly
                355                 360                 365

Leu Ala Phe Ile Ala Tyr Pro Lys Ala Val Thr Met Met Pro Leu Pro
            370                 375                 380

Thr Phe Trp Ser Ile Leu Phe Phe Ile Met Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Val Phe Ile
            420                 425                 430

Ala Ile Leu Cys Ser Ile Ser Tyr Leu Leu Gly Leu Ser Met Val Thr
            435                 440                 445

Glu Gly Gly Met Tyr Val Phe Gln Leu Phe Asp Tyr Tyr Ala Ala Ser
    450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510

Pro Val Leu Cys Ala Gly Cys Phe Ile Phe Ser Leu Val Lys Tyr Val
            515                 520                 525

Pro Leu Thr Tyr Asn Lys Val Tyr Val Tyr Pro Asp Trp Ala Ile Gly
    530                 535                 540

Leu Gly Trp Gly Leu Ala Leu Ser Ser Met Val Cys Ile Pro Leu Val
545                 550                 555                 560

Ile Ala Ile Leu Leu Cys Arg Thr Glu Gly Pro Phe Arg Val Arg Ile
                565                 570                 575

Gln Tyr Leu Ile Thr Pro Arg Glu Pro Asn Arg Trp Ala Val Glu Arg
            580                 585                 590

Glu Gly Ala Thr Pro Phe His Ser Arg Thr Ser Leu Val Met Asn Gly
            595                 600                 605

Ala Leu Met Lys Pro Ser His Val Ile Val Glu Thr Met Met
    610                 615                 620

```
<210> SEQ ID NO 3
<211> LENGTH: 1866
<212> TYPE: DNA
<213> ORGANISM: Rattus norvegicus

<400> SEQUENCE: 3
atggccacca aggagaagct tcaatgtctg aaagacttcc acaaagacat cctgaagcct      60
tctccaggga gagcccagg cacgcggcct gaggatgagg ctgatgggaa gcccctcag      120 agggagaagt ggtccagcaa gatcgacttt gtgctgtctg tggccggagg cttcgtgggt      180
ttgggcaatg tctggcgttt cccgtacctc tgctacaaaa atggtggagg tgcattcctc      240
ataccgtatt ttattttcct gtttgggagc ggcctgcctg tgttttttcct ggaggtcatc      300 ataggccagt acacctcaga aggggcatc acctgctggg agaagatctg ccccttgttc      360
tctggcattg gctacgcgtc catcgtcatc gtgtccctcc tgaatgtgta ctacatcgtc      420
atcctggcct gggccacata ctacctattc agtctttcc agaaggatct tccctgggcc      480
cactgcaacc atagctggaa cacgccacag tgcatggagg acaccctgcg taggaacgag      540
```

```
agtcactggg tctcccttag cgccgccaac ttcacttcgc ctgtgatcga gttctgggag    600
cgcaacgtgc tcagcctgtc ctccggaatc gaccacccag gcagtctgaa atgggacctc    660
gcgctctgcc tcctcttagt ctggctcgtc tgttttttct gcatctggaa gggtgttcgg    720
tccacaggca aggttgtcta cttcactgct actttcccgt ttgccatgct tctggtgctg    780
ctggtccgtg gactgaccct gccaggtgct ggtgaaggca tcaaattcta cctgtaccct    840
aacatcagcc gccttgagga cccacaggtg tggatcgacg ctggaactca gatattcttt    900
tcctacgcta tctgcctggg ggccatgacc tcactgggaa gctataacaa gtacaagtat    960
aactcgtaca gggactgtat gctgctggga tgcctgaaca gtggtaccag ttttgtgtct   1020
ggcttcgcaa ttttttccat cctgggcttc atggcacaag agcaagggt ggacattgct   1080
gatgtggctg agtcaggtcc tggcttggcc ttcattgcct acccaaaagc tgtgaccatg   1140
atgccgctgc ccaccttttg gtccattctg tttttttatta tgctcctctt gcttggactg   1200
gacagccagt ttgttgaagt cgaaggacag atcacatcct tggttgatct ttacccgtcc   1260
ttcctaagga agggttatcg tcgggaaatc ttcattgcca tcgtgtgcag catcagctac   1320
ctgctggggc tgacgatggt gacggagggt ggcatgtatg tgtttcaact ctttgactac   1380
tatgcagcta gtggtgtatg cctttttgtgg gtcgcattct ttgaatgttt tgttattgcc   1440
tggatatatg gcggtgataa cttatatgac ggtattgagg acatgatcgg ctatcggcct   1500
ggaccctgga tgaagtacag ctgggctgtc atcactccag ctctctgtgt ggatgtttc    1560
atcttctctc tcgtcaagta tgtacccctg acctacaaca agtctaccg gtaccctgat   1620
tgggcaatcg gctgggctg gggcctggcc ctttcctcca tggtgtgtat ccccttggtc   1680
attgtcatcc tcctctgccg gacggaggga ccgctccgcg tgagaatcaa atacctgata   1740
accccccaggg agcccaaccg ctgggctgtg gagcgtgaag gggctacgcc ctttcactcc   1800
agagcaaccc tcatgaacgg tgcactcatg aaacccagtc acgtcattgt ggagaccatg   1860
atgtga                                                              1866
```

<210> SEQ ID NO 4
<211> LENGTH: 621
<212> TYPE: PRT
<213> ORGANISM: Rattus norvegicus

<400> SEQUENCE: 4

Met Ala Thr Lys Glu Lys Leu Gln Cys Leu Lys Asp Phe His Lys Asp
 1               5                   10                  15

Ile Leu Lys Pro Ser Pro Gly Lys Ser Pro Gly Thr Arg Pro Glu Asp
            20                  25                  30

Glu Ala Asp Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp

```
                130             135             140
Ala Thr Tyr Tyr Leu Phe Gln Ser Phe Gln Lys Asp Leu Pro Trp Ala
145                 150                 155                 160

His Cys Asn His Ser Trp Asn Thr Pro Gln Cys Met Glu Asp Thr Leu
                165                 170                 175

Arg Arg Asn Glu Ser His Trp Val Ser Leu Ser Ala Ala Asn Phe Thr
                180                 185                 190

Ser Pro Val Ile Glu Phe Trp Glu Arg Asn Val Leu Ser Leu Ser Ser
                195                 200                 205

Gly Ile Asp His Pro Gly Ser Leu Lys Trp Asp Leu Ala Leu Cys Leu
                210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
                260                 265                 270

Gly Ile Lys Phe Tyr Leu Tyr Pro Asn Ile Ser Arg Leu Glu Asp Pro
                275                 280                 285

Gln Val Trp Ile Asp Ala Gly Thr Gln Ile Phe Phe Ser Tyr Ala Ile
                290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Ile Phe Ser Ile Leu Gly Phe Met Ala
                340                 345                 350

Gln Glu Gln Gly Val Asp Ile Ala Asp Val Ala Glu Ser Gly Pro Gly
                355                 360                 365

Leu Ala Phe Ile Ala Tyr Pro Lys Ala Val Thr Met Met Pro Leu Pro
                370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Ile Phe Ile
                420                 425                 430

Ala Ile Val Cys Ser Ile Ser Tyr Leu Leu Gly Leu Thr Met Val Thr
                435                 440                 445

Glu Gly Gly Met Tyr Val Phe Gln Leu Phe Asp Tyr Tyr Ala Ala Ser
450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
                500                 505                 510

Pro Ala Leu Cys Val Gly Cys Phe Ile Phe Ser Leu Val Lys Tyr Val
                515                 520                 525

Pro Leu Thr Tyr Asn Lys Val Tyr Arg Tyr Pro Asp Trp Ala Ile Gly
                530                 535                 540

Leu Gly Trp Gly Leu Ala Leu Ser Ser Met Val Cys Ile Pro Leu Val
545                 550                 555                 560
```

```
Ile Val Ile Leu Leu Cys Arg Thr Glu Gly Pro Leu Arg Val Arg Ile
            565                 570                 575

Lys Tyr Leu Ile Thr Pro Arg Glu Pro Asn Arg Trp Ala Val Glu Arg
        580                 585                 590

Glu Gly Ala Thr Pro Phe His Ser Arg Ala Thr Leu Met Asn Gly Ala
        595                 600                 605

Leu Met Lys Pro Ser His Val Ile Val Glu Thr Met Met
610                 615                 620

<210> SEQ ID NO 5
<211> LENGTH: 1866
<212> TYPE: DNA
<213> ORGANISM: Mus musculus

<400> SEQUENCE: 5
atggccacga aggagaagct gcaatgtctg aaagacttcc acaaagacat cctgaagcct      60
tctccaggga gagcccagg cacacggcct gaagatgagg cggacgggaa gcccccctcag     120 agggagaagt ggtccagcaa gatcgacttt gtgctgtctg tggccggagg cttcgtgggt     180
ttgggcaacg tctggcgttt cccgtacctc tgctacaaaa atggtggagg tgcgttcctc     240
ataccgtatt ttattttcct gtttgggagc ggcctgcctg tgttttctt ggaggtcatc      300 ataggccagt acacatcaga aggggggcatc acctgctggg agaagatctg tcctttgttc    360
tctggcattg gctacgcatc catcgtcatt gtgtccctcc tgaacgtgta ctacatcgtc     420
atcctggcct gggccacata ctacctattc cactcttttcc agaaggatct tccctgggcc    480
cactgcaacc atagctggaa cacaccacag tgcatggagg acaccctgcg taggaacgag    540
agtcactggg tctcccttag cactgccaac ttcacctcac ccgtcatcga gttctgggag     600
cgcaatgtgc tcagcctgtc ctccggaatc gacaacccag gcagtctgaa atgggaccctc   660 gcgctctgcc tcctcttagt ctggctcgtc tgttttttct gcatctggaa gggtgttcga    720
tccacaggca aggttgtcta cttcaccgct actttcccgt ttgccatgct tctggtgctg     780
ctggtccgtg gactgaccct gccaggtgct ggtgaaggca tcaaattcta cctgtacccct    840 gacatcagcc gccttgggga cccacaggtg tggatcgacg ctggaactca gatattcttt     900
tcctacgcaa tctgcctggg ggccatgacc tcactgggaa gctataacaa gtacaagtat    960
aactcgtaca gggactgtat gctgctggga tgcctgaaca gtggtaccag ttttgtgtct    1020
ggcttcgcaa ttttttccat cctgggcttc atggcacaag agcaagggt ggacattgct    1080 gatgtggctg agtcaggtcc tggcttggcc ttcattgcct acccaaaagc tgtaaccatg    1140
atgccgctgc ccacctttg gtctattctg ttttcatta tgctcctctt gcttggactg      1200
gacagccagt tgttgaagt cgaaggacag atcacatcct tggttgatct ttacccgtcc    1260
ttcctaagga agggttatcg tcgggaaatc ttcatagcca tcttgtgtag catcagctac    1320 ctgctgggc tgacgatggt gacgagggt ggcatgtatg tgtttcaact ctttgactac      1380
tatgcagcta gtggtgtatg cctttttgtgg gttgcattct ttgaatgttt tgttattgcc   1440
tggatatatg gcggtgataa cttatatgac ggtattgagg acatgattgg ctatcggcct    1500
gggccctgga tgaagtacag ctgggctgtc atcactccag ctctttgtgt tggatgtttc    1560
gtcttctcgc ttgtcaagta tgtacccctg acctacaaca agtgtaccgt tacccggat    1620 tgggcaattg gctgggctg gggcctggcc ctttcctcca tgctgtgtat ccccttggtc    1680
attgtcatcc tcctctgccg gacggaggga ccgctccgcg tgagaatcaa ataccctgata  1740
```

-continued

```
acccccaggg agcccaaccg ctgggctgtg gagcgtgaag gggccacacc ctttcactcc    1800
cgagtaaccc tcatgaacgg cgcactcatg aaacccagtc acgtcattgt ggagaccatg    1860
atgtga                                                               1866
```

<210> SEQ ID NO 6
<211> LENGTH: 621
<212> TYPE: PRT
<213> ORGANISM: Mus musculus
<400> SEQUENCE: 6

```
Met Ala Thr Lys Glu Lys Leu Gln Cys Leu Lys Asp Phe His Lys Asp
 1               5                  10                  15

Ile Leu Lys Pro Ser Gly Lys Pro Gly Thr Arg Pro Glu Asp
            20                  25                  30

Glu Ala Asp Gly Lys Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Ala Phe Leu
 65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp
    130                 135                 140

Ala Thr Tyr Tyr Leu Phe His Ser Phe Gln Lys Asp Leu Pro Trp Ala
145                 150                 155                 160

His Cys Asn His Ser Trp Asn Thr Pro Gln Cys Met Glu Asp Thr Leu
                165                 170                 175

Arg Arg Asn Glu Ser His Trp Val Ser Leu Ser Thr Ala Asn Phe Thr
            180                 185                 190

Ser Pro Val Ile Glu Phe Trp Glu Arg Asn Val Leu Ser Leu Ser Ser
        195                 200                 205

Gly Ile Asp Asn Pro Gly Ser Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asp Ile Ser Arg Leu Gly Asp Pro
        275                 280                 285

Gln Val Trp Ile Asp Ala Gly Thr Gln Ile Phe Phe Ser Tyr Ala Ile
    290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Ile Phe Ser Ile Leu Gly Phe Met Ala
            340                 345                 350
```

```
Gln Glu Gln Gly Val Asp Ile Ala Asp Val Ala Glu Ser Gly Pro Gly
            355                 360                 365
Leu Ala Phe Ile Ala Tyr Pro Lys Ala Val Thr Met Met Pro Leu Pro
        370                 375                 380
Thr Phe Trp Ser Ile Leu Phe Phe Ile Met Leu Leu Leu Gly Leu
385                 390                 395                 400
Asp Ser Gln Phe Val Glu Val Glu Gly Gln Ile Thr Ser Leu Val Asp
                405                 410                 415
Leu Tyr Pro Ser Phe Leu Arg Lys Gly Tyr Arg Arg Glu Ile Phe Ile
            420                 425                 430
Ala Ile Leu Cys Ser Ile Ser Tyr Leu Leu Gly Leu Thr Met Val Thr
        435                 440                 445
Glu Gly Gly Met Tyr Val Phe Gln Leu Phe Asp Tyr Tyr Ala Ala Ser
    450                 455                 460
Gly Val Cys Leu Leu Trp Val Ala Phe Phe Glu Cys Phe Val Ile Ala
465                 470                 475                 480
Trp Ile Tyr Gly Gly Asp Asn Leu Tyr Asp Gly Ile Glu Asp Met Ile
                485                 490                 495
Gly Tyr Arg Pro Gly Pro Trp Met Lys Tyr Ser Trp Ala Val Ile Thr
            500                 505                 510
Pro Ala Leu Cys Val Gly Cys Phe Val Phe Ser Leu Val Lys Tyr Val
        515                 520                 525
Pro Leu Thr Tyr Asn Lys Val Tyr Arg Tyr Pro Asp Trp Ala Ile Gly
    530                 535                 540
Leu Gly Trp Gly Leu Ala Leu Ser Ser Met Leu Cys Ile Pro Leu Val
545                 550                 555                 560
Ile Val Ile Leu Leu Cys Arg Thr Glu Gly Pro Leu Arg Val Arg Ile
                565                 570                 575
Lys Tyr Leu Ile Thr Pro Arg Glu Pro Asn Arg Trp Ala Val Glu Arg
            580                 585                 590
Glu Gly Ala Thr Pro Phe His Ser Arg Val Thr Leu Met Asn Gly Ala
        595                 600                 605
Leu Met Lys Pro Ser His Val Ile Val Glu Thr Met Met
    610                 615                 620

<210> SEQ ID NO 7
<211> LENGTH: 1863
<212> TYPE: DNA
<213> ORGANISM: Homo sapiens

<400> SEQUENCE: 7
atggccacca aggagaagct gcagtgtctg aaagatttcc acaaggacat cctgaagccc      60
tcaccaggga agagcccagg cacgcggcct gaggacgagg ctgagggaaa acctccgcag     120
agggagaagt ggtctagcaa gatcgacttt gtgctctctg tggctggcgg cttcgtgggc     180
ttgggcaacg tctggcgctt cccgtacctc tgctacaaga atggtggagg tgcgtttctc     240
ataccgtatt ttattttcct gtttgggagc ggcctgcctg tgttttttctt ggagatcatc     300 ataggccagt acacctctga agggggcatc acctgctggg aaaagatctg ccccttgttc     360
tctggtatcg gctatgcctc cgttgtaatt gtgtccctcc tgaatgtcta ctacatcgtc     420
atcctggcct gggccacata ctacctgttc cagtccttcc agaaggagct gccctgggca     480
cactgcaacc acagctggaa cacacctcac tgcatggagg acaccatgcg caagaacaag     540
agtgtctgga tcaccatcag ctccaccaac ttcacctccc ctgtcatcga gttctgggag     600
```

-continued

```
cgcaacgtgc tgagcttgtc ccctggaatc gaccacccag ctctctgaa atgggacctc     660
gctctctgcc ttcttttagt ctggctagtg tgtttcttct gcatctggaa gggcgtcagg    720
tccactggga aggtcgtcta cttcacagcc acttttccat cgccatgct cctggtgctg     780
ctggtccgag gctgacgct gccgggcgcg ggcgcaggca tcaagttcta tctgtatcct     840
gacatcaccc gccttgagga cccacaggtg tggattgacg ctgggactca gatattcttc    900
tcttatgcca tctgcctggg ggctatgacc tcgctgggga gctacaacaa gtacaagtat    960
aactcgtaca gggactgtat gctgctggga tgcctgaaca gtggtaccag ttttgtgtct   1020
ggcttcgcaa ttttttccat cctgggcttc atggcacaag agcaagggt ggacattgct    1080
gatgtggctg agtcaggtcc tggcctggcc ttcattgcct acccaaaagc tgtgacaatg   1140
atgccgctgc ccacattttg gtccattctt tttttatta tgcttctctt gcttggactg    1200
gatagccagt tgttgaagt tgaaggacag atcacatcct tggttgatct ttacccatcc    1260
ttcctaagga agggttatcg tcgggaaatc ttcatcgcct tcgtgtgtag catcagctac   1320
ctgctggggc tgacgatggt gacggagggt ggcatgtatg tgtttcagct ctttgactac   1380
tatgcagcta gcggtgtatg ccttttgtgg gttgcattct ttgaatgttt tgttattgcc   1440
tggatatatg gaggtgataa cctttatgat ggtattgagg acatgattgg ctatcggccc   1500
gggccctgga tgaagtacag ctgggctgtg atcactccag ttctctgtgt tggatgtttc   1560
atcttctcgc tcgtcaagta cgtaccctg acctacaaca aacatacgt gtaccccaac    1620
tgggccattg gctgggctg gagcctggcc ctttcctcca tgctctgcgt tcccttggtc    1680
atcgtcatcc gcctctgcca gactgagggg ccgttccttg tgagagtcaa gtacctgctg   1740
accccaaggg aacccaaccg ctgggctgtg agcgcgagg gagccacacc ttacaactct    1800
cgcaccgtca tgaacggcgc tctcgtgaaa ccgacccaca tcattgtgga gaccatgatg   1860
tga                                                                 1863
```

<210> SEQ ID NO 8
<211> LENGTH: 620
<212> TYPE: PRT
<213> ORGANISM: Homo sapiens

<400> SEQUENCE: 8

```
Met Ala Thr Lys Glu Lys Leu Gln Cys Leu Lys Asp Phe His Lys Asp
 1               5                  10                  15

Ile Leu Lys Pro Ser Pro Gly Lys Ser Pro Gly Thr Arg Pro Glu Asp
            20                  25                  30

Glu Ala Glu Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Ile Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Val
        115                 120                 125

Val Ile Val Ser Leu Leu Asn Val Tyr Tyr Ile Val Ile Leu Ala Trp
    130                 135                 140
```

```
Ala Thr Tyr Tyr Leu Phe Gln Ser Phe Gln Lys Glu Leu Pro Trp Ala
145                 150                 155                 160

His Cys Asn His Ser Trp Asn Thr Pro His Cys Met Glu Asp Thr Met
            165                 170                 175

Arg Lys Asn Lys Ser Val Trp Ile Thr Ile Ser Ser Thr Asn Phe Thr
            180                 185                 190

Ser Pro Val Ile Glu Phe Trp Glu Arg Asn Val Leu Ser Leu Ser Pro
            195                 200                 205

Gly Ile Asp His Pro Gly Ser Leu Lys Trp Asp Leu Ala Leu Cys Leu
            210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
            245                 250                 255

Leu Leu Val Leu Leu Val Arg Gly Leu Thr Leu Pro Gly Ala Gly Ala
            260                 265                 270

Gly Ile Lys Phe Tyr Leu Tyr Pro Asp Ile Thr Arg Leu Glu Asp Pro
            275                 280                 285

Gln Val Trp Ile Asp Ala Gly Thr Gln Ile Phe Phe Ser Tyr Ala Ile
290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
            325                 330                 335

Ser Phe Val Ser Gly Phe Ala Ile Phe Ser Ile Leu Gly Phe Met Ala
            340                 345                 350

Gln Glu Gln Gly Val Asp Ile Ala Asp Val Ala Glu Ser Gly Pro Gly
            355                 360                 365

Leu Ala Phe Ile Ala Tyr Pro Lys Ala Val Thr Met Met Pro Leu Pro
            370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
            405                 410                 415

Leu Tyr Pro Ser Phe Leu Arg Lys Gly Tyr Arg Arg Glu Ile Phe Ile
            420                 425                 430

Ala Phe Val Cys Ser Ile Ser Tyr Leu Leu Gly Leu Thr Met Val Thr
            435                 440                 445

Glu Gly Gly Met Tyr Val Phe Gln Leu Phe Asp Tyr Tyr Ala Ala Ser
            450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
            485                 490                 495

Gly Tyr Arg Pro Gly Pro Trp Met Lys Tyr Ser Trp Ala Val Ile Thr
            500                 505                 510

Pro Val Leu Cys Val Gly Cys Phe Ile Phe Ser Leu Val Lys Tyr Val
            515                 520                 525

Pro Leu Thr Tyr Asn Lys Thr Tyr Val Tyr Pro Asn Trp Ala Ile Gly
            530                 535                 540

Leu Gly Trp Ser Leu Ala Leu Ser Ser Met Leu Cys Val Pro Leu Val
545                 550                 555                 560
```

```
Ile Val Ile Arg Leu Cys Gln Thr Glu Gly Pro Phe Leu Val Arg Val
                565             570                 575

Lys Tyr Leu Leu Thr Pro Arg Glu Pro Asn Arg Trp Ala Val Glu Arg
            580             585                 590

Glu Gly Ala Thr Pro Tyr Asn Ser Arg Thr Val Met Asn Gly Ala Leu
            595             600             605

Val Lys Pro Thr His Ile Ile Val Glu Thr Met Met
            610             615             620
```

METHOD FOR RECOMBINANT PRODUCTION OF A DESIRED POLYPEPTIDE USING A MAMMALIAN CELL CO-EXPRESSING A TAURINE TRANSPORTER POLYPEPTIDE

CROSS-REFERENCE TO RELATED APPLICATIONS

This application is a National Stage application of PCT/JP2007/058049, filed Apr. 12, 2007, which claims priority from Japanese application JP 2006-110467, filed Apr. 13, 2006.

TECHNICAL FIELD

The present invention relates to a hamster taurine transporter and a gene encoding the hamster taurine transporter, as well as a method of producing a polypeptide using a cell which strongly expresses a taurine transporter.

BACKGROUND ART

When proteins useful as pharmaceuticals are produced with the recombinant DNA technique, use of animal cells enables complicated post-translational modification and folding which prokaryotic cells can not perform. Therefore, animal cells are frequently used as host cells for producing recombinant proteins.

Recently, a large number of biopharmaceuticals, such as antibodies and physiologically active proteins, have been developed. Techniques that permit efficient production of recombinant proteins by animal cells lead to cost reduction of biopharmaceuticals and promise their stable supply to patients.

Under these circumstances, a method of protein production with higher production efficiency is desired.

Taurine is a type of amino acid present in high concentrations in fish, shell fish and mollusks and is an important nutrient for the growth of mammals. Although taurine is not used in protein synthesis, it has many functions such as normalization of hypercholesterolemia, lowering of blood pressure, detoxication effect, maintenance of immune function, stabilization of biological membranes, regulation of neural excitability, antioxidation, etc. It is known that taurine contributes to osmoregulation and stabilization of cell membrane in cultured cells (Non-Patent Document 1). However, addition of taurine to the medium of astrocyte primary culture where taurine transporter was functioning did not increase taurine uptake into cells (Non-Patent Document 2). Thus, addition of taurine to the medium alone was insufficient.

On the other hand, it is totally unknown whether or not uptake of taurine and other amino acids into cultured cells via taurine transporter contributes to improvement of the production of a desired recombinant protein in the cultured cells.

Several taurine transporters (human: Non-Patent Document 3; mouse: Non-Patent Document 4; and rat: Non-Patent Document 5) and their involvement in the uptake of taurine and other amino acids (e.g., β-alanine) into cells are known (Non-Patent Document 6). However, with respect to hamster taurine transporter, even its existence has not been known yet.
[Non-Patent Document 1]
Ian Henry Lambert, Neurochemical Research (2004) 29(1), 27-63
[Non-Patent Document 2]
Journal of Neurochemistry (2000), 75(3), 919-924
[Non-Patent Document 3]
Uchida, S. et al., Proc. Natl. Acad. Sci. U.S.A. (1992) 89 (17), 8230-8234
[Non-Patent Document 4]
Liu, Q. R. et al., Proc. Natl. Acad. Sci. U.S.A. (1992) 89 (24), 12145-12149
[Non-Patent Document 5]
Smith, K. E. et al., Mol. Pharmacol. (1992) 42 (4), 563-569
[Non-Patent Document 6]
Ryo Shioda et al., Investigative Opthalmology & Visual Science (2002) 43 (9), 2916

DISCLOSURE OF THE INVENTION

Problem for Solution by the Invention

It is an object of the present invention to provide a method which is capable of producing a natural or recombinant protein at low cost.

Means to Solve the Problem

As a result of extensive and intensive researches toward the solution of the above problem, the present inventors have found that it is possible to increase the yield of a desired polypeptide by using a cell that strongly expresses a taurine transporter. Thus, the present invention has been achieved.

The present invention may be summarized as follows.
(1) A method of producing a polypeptide, comprising culturing a cell which strongly expresses a taurine transporter and has a transferred DNA encoding a desired polypeptide and thereby allowing the cell to produce said polypeptide.
(2) The method of (1) above, wherein the cell which strongly expresses a taurine transporter is a cell into which a DNA encoding the taurine transporter has been transferred.
(3) The method of (2) above, wherein the cell is Chinese hamster ovary cells.
(4) The method of any one of (1) to (3) above, wherein the desired polypeptide is an antibody.
(5) The method of any one of (2) to (4) above, wherein the DNA encoding the taurine transporter is any one of the following (a) to (e):
  (a) a DNA encoding a polypeptide having the amino acid sequence as shown in SEQ ID NO: 2, 4, 6 or 8;
  (b) a DNA encoding a polypeptide which has an amino acid sequence derived from the amino acid sequence as shown in SEQ ID NO: 2, 4, 6 or 8 by substitution, deletion, addition and/or insertion of one or more amino acid residues and yet has taurine transporter activity;
  (c) a DNA encoding a polypeptide having 70% or more amino acid sequence homology with the amino acid sequence as shown in SEQ ID NO: 2, 4, 6 or 8 and yet having taurine transporter activity;
  (d) a DNA having the nucleotide sequence as shown in SEQ ID NO: 1, 3, 5 or 7;
  (e) a DNA which hybridizes to a DNA complementary to a DNA having the nucleotide sequence as shown in SEQ ID NO: 1, 3, 5 or 7 under stringent conditions and yet encodes a polypeptide having taurine transporter activity.
(6) The method of any one of (1) to (5) above, comprising culturing the cells in a medium with a taurine concentration of 0 to 100 g/L.
(7) A method of preparing a pharmaceutical containing a polypeptide prepared by the method of any one of (1) to (6) above.
(8) A DNA encoding a taurine transporter, which is any one of the following (a) to (e), provided that DNA having the nucleotide sequence as shown in SEQ ID NO: 3, DNA having the nucleotide sequence as shown in SEQ ID NO: 5, and DNA having the nucleotide sequence as shown in SEQ ID NO: 7 are excluded:
(a) a DNA encoding a polypeptide having the amino acid sequence as shown in SEQ ID NO: 2;
(b) a DNA encoding a polypeptide which has an amino acid sequence derived from the amino acid sequence as shown in SEQ ID NO: 2 by substitution, deletion, addition and/or insertion of one or more amino acid residues and yet has taurine transporter activity;
(c) a DNA encoding a polypeptide having 97% or more amino acid sequence homology with the amino acid sequence as shown in SEQ ID NO: 2 and yet having taurine transporter activity;
(d) a DNA having the nucleotide sequence as shown in SEQ ID NO: 1;
(e) a DNA which hybridizes to a DNA complementary to a DNA having the nucleotide sequence as shown in SEQ ID NO: 1 under stringent conditions and yet encodes a polypeptide having taurine transporter activity.
(9) A polypeptide which is any one of the following (A) to (E), provided that a polypeptide having the amino acid sequence as shown in SEQ ID NO: 4, a polypeptide having the amino acid sequence as shown in SEQ ID NO: 6, and a polypeptide having the amino acid sequence as shown in SEQ ID NO: 8 are excluded:
(A) a polypeptide having the amino acid sequence as shown in SEQ ID NO: 2;
(B) a polypeptide which has an amino acid sequence derived from the amino acid sequence as shown in SEQ ID NO: 2 by substitution, deletion, addition and/or insertion of one or more amino acid residues and yet has taurine transporter activity;
(C) a polypeptide having 97% or more amino acid sequence homology with the amino acid sequence as shown in SEQ ID NO: 2 and yet having taurine transporter activity;
(D) a polypeptide encoded by a DNA having the nucleotide sequence as shown in SEQ ID NO: 1;
(E) a polypeptide encoded by a DNA which hybridizes to a DNA complementary to a DNA having the nucleotide sequence as shown in SEQ ID NO: 1 under stringent conditions and yet encodes a polypeptide having taurine transporter activity.
(10) A recombinant vector comprising the DNA of (8) above.
(11) A cell into which the DNA of (8) above has been transferred.
(12) A cell which strongly expresses a taurine transporter and yet has a transferred DNA encoding a desired polypeptide.
(13) A cell into which a DNA encoding a taurine transporter has been transferred.

Effect of the Invention

According to the present invention, it has become possible to produce a desired polypeptide at low cost.

The present specification encompasses the contents disclosed in the specification and/or the drawings of Japanese Patent Application No. 2006-110467 based on which the present patent application claims priority.

BRIEF DESCRIPTION OF THE DRAWINGS

FIG. 1 shows the nucleotide sequence of a newly cloned, CHO cell-derived hamster taurine transporter gene (SEQ ID NO:1) and the amino acid sequence deduced therefrom (SEQ ID NO: 2).

BEST MODE FOR CARRYING OUT THE INVENTION

Figure 2:
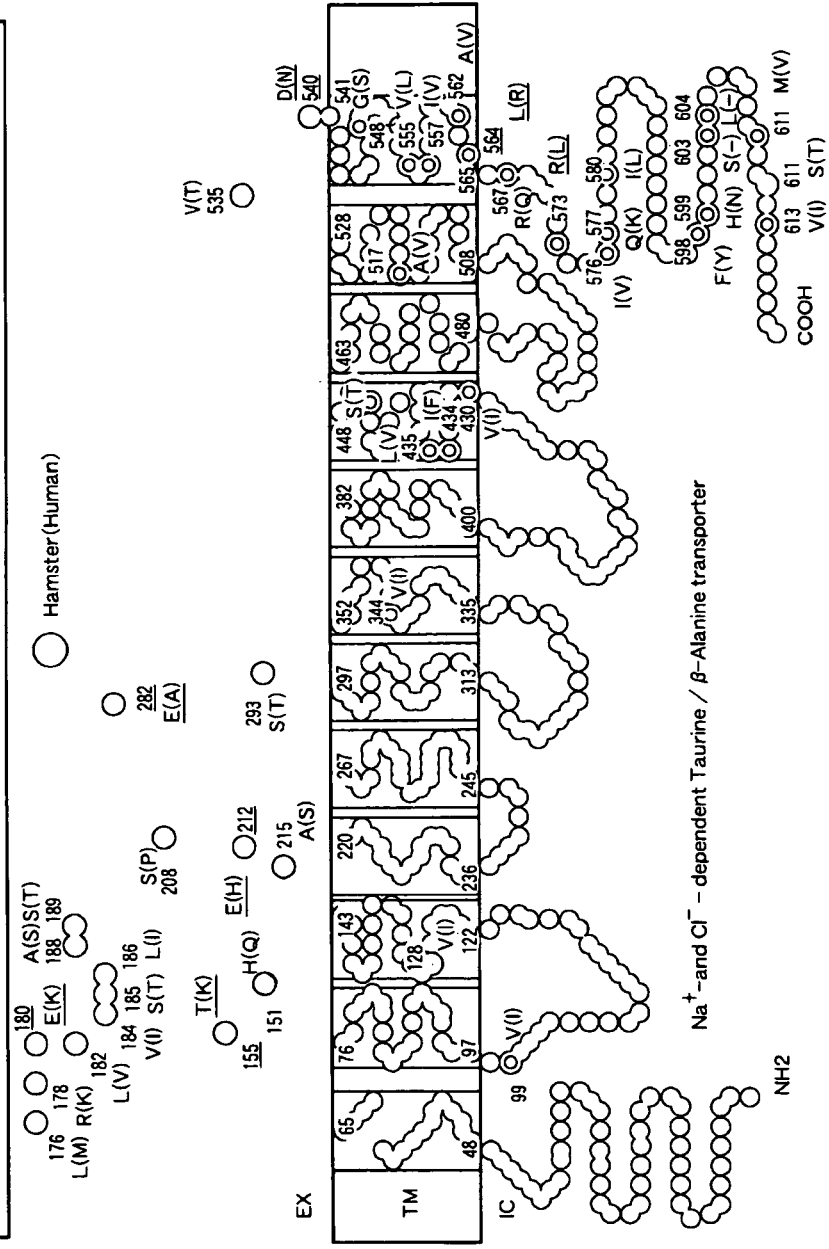
FIG. 2 is a taurine transporter membrane topology which was created based on the transmembrane regions and orientations predicted by TMpred program from the amino acid sequence of a newly cloned, CHO cell-derived hamster TauT with reference to FIG. 5 of Shinichi Uchida et al., Proc. Natl. Acad. Sci. USA Vol. 89, pp. 8230-8234, September 1992. Mark ⊙ indicates hamster TauT specific amino acid residues. A large number of amino acid residues different from those in human TauT are present in the 2nd loop (EX: extra-cell membrane region), the 12th transmembrane region (TM) and the C-terminal (IC: intracellular region).

Hereinbelow, embodiments of the present invention will be described in more detail.

The present invention provides a method of producing a polypeptide, comprising culturing a cell which strongly expresses a taurine transporter and has a transferred DNA encoding a desired polypeptide and thereby allowing the cell to produce the polypeptide.

In the method of the present invention, the cell may be either a natural cell capable of producing the desired polypeptide or a transformed cell into which a DNA encoding the desired polypeptide has been transferred. Preferably, a transformed cell into which a DNA encoding the desired polypeptide has been transferred is used.

In the method of the present invention, the desired polypeptide is not particularly limited. The polypeptide may be any polypeptide such as an antibody (e.g., anti-IL-6 receptor antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody, anti-VLA4 antibody, and the like) or a physiologically active protein (e.g., granulocyte-colony stimulating factor (G-CSF), granulocyte macrophage-colony stimulating factor (GM-CSF), erythropoietin, interferon, interleukin such as IL-1 or IL-6, t-PA, urokinase, serum albumin, blood coagulation factor, PTH, and the like). An antibody is particularly preferred, and may be any antibody such as a natural antibody, a low molecular sized antibody (e.g., Fab, scFv, sc(Fv)2), a chimeric antibody, a humanized antibody, etc.

The present inventors have found that, by using a cell which strongly expresses a taurine transporter, intracellular uptake of not only taurine and β-alanine but also glutamine is specifically promoted via the strongly expressed taurine transporter.

It is known that taurine transporter is a membrane protein having the function of taking up amino acids (such as taurine and β-alanine) into cells. However, it is not known that cells begin to take up glutamine specifically when they are allowed to express a taurine transporter strongly. Since it is known that glutamine is involved in antibody production in hybridomas (Yeon-Ho Jeong et al, Enzyme and Microbial Technology (1995) 17, 47-55), the effect of enhancement of protein (e.g., antibody) production by a cell which has been allowed to strongly express a taurine transporter may be caused by the taurine transporter-mediated specific uptake of glutamine into cells.

A cell which strongly expresses a taurine transporter is not particularly limited as long as the cell has an increased expression level of a taurine transporter compared to a corresponding natural cell. The natural cell is not particularly limited. A cell which is used as a host in the production of a recombinant protein (e.g., CHO cells) may be used.

As a cell which strongly expresses a taurine transporter, a cell into which a taurine transporter gene has been artificially transferred may be given. A cell into which a taurine transporter gene has been artificially transferred can be prepared by methods known to those skilled in the art. For example, such a cell may be prepared by incorporating a taurine transporter gene into a vector and transforming the vector into a cell.

As a taurine transporter to be strongly expressed in a cell, a taurine transporter derived from any organism may be used. Specifically, a taurine transporter derived from human or a rodent (such as mouse, rat or hamster) may be used. Preferably, a taurine transporter derived from human, a rodent or the same species as the host cell may be used. For example, when the cell which is allowed to strongly express a taurine transporter is Chinese hamster ovary cells (CHO cells), the taurine transporter is preferably derived from human or hamster.

Further, as a taurine transporter gene to be strongly expressed in a cell, any one of the following DNAs (a) to (e) encoding a taurine transporter may be used.
(a) a DNA encoding a polypeptide having the amino acid sequence as shown in SEQ ID NO: 2, 4, 6 or 8;
(b) a DNA encoding a polypeptide which has an amino acid sequence derived from the amino acid sequence as shown in SEQ ID NO: 2, 4, 6 or 8 by substitution, deletion, addition and/or insertion of one or more amino acid residues and yet has taurine transporter activity;
(c) a DNA encoding a polypeptide having 70% or more amino acid sequence homology with the amino acid sequence as shown in SEQ ID NO: 2, 4, 6 or 8 and yet having taurine transporter activity;
(d) a DNA having the nucleotide sequence as shown in SEQ ID NO: 1, 3, 5 or 7;
(e) a DNA which hybridizes to a DNA complementary to a DNA having the nucleotide sequence as shown in SEQ ID NO: 1, 3, 5 or 7 under stringent conditions and yet encodes a polypeptide having taurine transporter activity.

The cell which strongly expresses a taurine transporter may be any cell. Preferably, CHO cells are used; CHO-dhfr- cells are particularly preferred.

Production of a desired polypeptide may be performed by transferring a gene encoding the desired polypeptide into a cell which strongly expresses a taurine transporter and culturing the resultant cell.

When a desired polypeptide is produced using a cell into which a taurine transporter gene has been artificially transferred, the order of the transfer of a taurine transporter gene and the transfer of a gene encoding a desired polypeptide is not particularly limited. A gene encoding a desired polypeptide may be transferred after the transfer of a taurine transporter gene. Alternatively, a taurine transporter gene may be transferred after the transfer of a gene encoding a desired polypeptide. It is also possible to transfer a taurine transporter gene and a gene encoding a desired polypeptide simultaneously.

A taurine transporter gene and a gene encoding a desired polypeptide may be transferred simultaneously in a single vector. Alternatively, they may be transferred separately using a plurality of vectors.

For culturing the cell which strongly expresses a taurine transporter, media used in conventional cell culture (preferably, animal cell culture) may be used. These media usually contain amino acids, vitamins, lipid factors, energy sources, osmotic regulators, iron sources and pH regulators. The contents of these components are usually as follows: amino acids 0.05-1500 mg/L, vitamins 0.001-10 mg/L, lipid factors 0-200 mg/L, energy sources 1-20 g/L, osmotic regulators 0.1-10000 mg/L, iron sources 0.1-500 mg/L, pH regulators 1-10000 mg/L, trace metal elements 0.00001-200 mg/L, surfactants 0-5000 mg/L, growth cofactors 0.05-10000 μg/L and nucleosides 0.001-50 mg/L. However, the contents are not limited to these ranges and may be appropriately selected depending on the type of the cell to be cultured, the type of the desired polypeptide, and so on.

In addition to these components, trace metal elements, surfactants, growth cofactors, nucleosides, and the like may be added.

Specific examples of such components include amino acids, such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine; vitamins, such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin $B_{12}$ and ascorbic acid, preferably, biotin, folic acid, lipoic acid, nicotinamide, calcium pantothenate, pyridoxal hydrochloride, riboflavin, thiamine hydrochloride, vitamin $B_{12}$ and ascorbic acid; lipid factors, such as choline chloride, choline tartrate, linoleic acid, oleic acid and cholesterol, preferably, choline chloride; energy sources, such as glucose, galactose, mannose, and fructose, preferably, glucose; osmotic regulators, such as sodium chloride, potassium chloride, and potassium nitrate, preferably, sodium chloride; iron sources, such as iron EDTA, ferric citrate, ferrous chloride, ferric chloride, ferrous sulfate, ferric sulfate, and ferric nitrate, preferably, ferric chloride, iron EDTA, and ferric citrate; and pH regulators, such as sodium hydrogencarbonate, calcium chloride, sodium dihydrogenphosphate, HEPES and MOPS, preferably, sodium hydrogencarbonate. Culture media containing any of these components may be given as examples.

Besides the above components, there may be added trace metal elements, such as copper sulfate, manganese sulfate, zinc sulfate, magnesium sulfate, nickel chloride, tin chloride, magnesium chloride and sodium subsilicate, preferably, copper sulfate, zinc sulfate and magnesium sulfate; surfactants, such as Tween 80 and Pluronic F68; growth cofactors, such as recombinant insulin, recombinant IGF-1, recombinant EGF, recombinant FGF, recombinant PDGF, recombinant TGF-α ethanolamine hydrochloride, sodium selenite, retinoic acid and putrescine dihydrochloride, preferably, sodium selenite, ethanolamine hydrochloride, recombinant IGF-1 and putrescine dihydrochloride; and nucleosides, such as deoxyadenosine, deoxycytidine, deoxyguanosine, adenosine, cytidine, guanosine and uridine. In preferable examples of above media, antibiotics, such as streptomycin, penicillin-G potassium and gentamicin, and pH-indicators, such as Phenol Red, may be contained.

The pH of the medium varies depending on the cell to be cultured. Generally, pH 6.8-7.6 is appropriate. In many cases, pH 7.0-7.4 is appropriate.

It is also possible to use a commercial medium for animal cell culture, e.g., D-MEM (Dulbecco's Modified Eagle Medium), D-MEM/F-12 1:1 Mixture (Dulbecco's Modified Eagle Medium Nutrient Mixture F-12), RPMI1640, CHO-S-SFMII (Invitrogen), CHO-SF (Sigma-Aldrich), EX-CELL 301 (JRH Biosciences), CD-CHO (Invitrogen), IS CHO-V (Irvine Scientific), PF-ACF-CHO (Sigma-Aldrich) or the like.

Alternatively, the medium may be a serum-free medium.

When the cell which strongly expresses a taurine transporter is CHO cells, CHO cells may be cultured by methods known to those skilled in the art. For example, CHO cells may be cultured usually in an atmosphere with a $CO_2$ concentration in the gas phase of 0 to 40%, preferably 2 to 10%, at 30 to 39° C., preferably about 37° C.

As is clear from the Examples described later, production of waste products (such as lactate) which turn to be cell growth inhibitory substances can be inhibited in a cell strongly expressing a taurine transporter. As a result, the cell shows the effect of maintaining a high survival ratio. The cell of the present invention is capable of culturing for three months or a still longer period.

Further, when a desired polypeptide, such as an antibody, is produced in cultured cells, the cells come into a highly concentrated state (about $1 \times 10^7$ cells/ml) at the late-stage of culture, and the influence of waste products such as lactate becomes extremely high. When a desired polypeptide is produced using the cell of the present invention, a high survival ratio is maintained even at the late-stage of culture, and an improvement can be expected in the yield of the desired polypeptide.

An appropriate culture period for producing a desired polypeptide using the cell of the present invention is usually 1 day to 3 months, preferably 1 day to 2 months, more preferably 1 day to 1 month.

With respect to various culture devices for animal cell culture, a fermentor type tank culture device, an air lift type culture device, a culture flask type culture device, a spinner flask type culture device, a microcarrier type culture device, a fluidized bed type culture device, a hollow fiber type culture device, a roller bottle type culture device, a packed bed type culture device, or the like may be used.

Culture may be performed by any culture method such as batch culture, fed-batch culture or continuous culture. Preferably, fed-batch culture or continuous culture is used. Fed-batch culture is more preferred.

When the cell of the present invention is cultured, taurine may be added to the medium in order to promote taurine uptake into cells. The concentration of taurine added to the medium is not particularly limited. The concentration is usually 0-100 g/L, preferably 0-20 g/L, more preferably 0-10 g/L.

When the polypeptide produced according to the method of the present invention has a biological activity useful as a pharmaceutical, it is possible to produce a pharmaceutical by mixing this polypeptide with pharmaceutically acceptable carriers or additives and formulating into a preparation.

Specific examples of pharmaceutically acceptable carriers and additives include water, organic solvents that are pharmaceutically acceptable, collagen, polyvinyl alcohol, polyvinylpyrrolidone, carboxyvinyl polymer, carboxymethylcellulose sodium, sodium polyacrylate, sodium alginate, water-soluble dextran, carboxymethyl starch sodium, pectin, methylcellulose, ethyl cellulose, xanthan gum, gum Arabic, casein, agar-agar, polyethylene glycol, diglycerin, glycerin, propylene glycol, petrolatum, paraffin, stearyl alcohol, stearic acid, human serum albumin (HSA), mannitol, sorbitol, lactose, and surfactants that are acceptable as pharmaceutical additives.

Actual additives may be selected from the above-mentioned additives singly or in combination according to the dosage form of the therapeutic of the present invention, but are not limited to those listed above. For example, when a polypeptide is used in an injectable formulation, the purified polypeptide may be dissolved in a solvent such as physiological saline, buffer or a glucose solution, and then an adsorption inhibitor such as Tween 80, Tween 20, gelatin or human serum albumin may be added to the solution. Alternatively, a freeze-dried agent may be used to prepare a dosage form which is dissolved and reconstituted prior to use. Examples of the excipient useful for freeze-drying include sugar alcohols and saccharides such as mannitol and glucose.

Effective doses of the polypeptide may be appropriately selected depending on the type of the polypeptide, the type of the disease to be treated or prevented, the age of the patient, the severity of the disease, etc. For example, when the polypeptide is anti-glypican antibody, the effective dose of anti-glypican antibody is selected within a range of 0.001 mg to 1000 mg per kg of body weight per administration. Alternatively, a dose of 0.01-100000 mg/body may be selected per patient. However, effective dose is not limited to these ranges.

The polypeptide may be administered either orally or parenterally, but parenteral administration is preferred. Specifically, injection (e.g., systemic or local administration by intravenous injection, intramuscular injection, intraperitoneal injection, subcutaneous injection, etc.), transnasal administration, transpulmonary administration, transdermal administration and the like may be enumerated.

The present invention provides a novel polypeptide which is any one of the following (A) to (E), provided that a polypeptide having the amino acid sequence as shown in SEQ ID NO: 4, a polypeptide having the amino acid sequence as shown in SEQ ID NO: 6, and a polypeptide having the amino acid sequence as shown in SEQ ID NO: 8 are excluded:

(A) a polypeptide having the amino acid sequence as shown in SEQ ID NO: 2;
(B) a polypeptide which has an amino acid sequence derived from the amino acid sequence as shown in SEQ ID NO: 2 by substitution, deletion, addition and/or insertion of one or more amino acid residues and yet has taurine transporter activity;
(C) a polypeptide having 97% or more amino acid sequence homology with the amino acid sequence as shown in SEQ ID NO: 2 and yet having taurine transporter activity;
(D) a polypeptide encoded by a DNA having the nucleotide sequence as shown in SEQ ID NO: 1; or
(E) a polypeptide encoded by a DNA which hybridizes to a DNA complementary to a DNA having the nucleotide sequence as shown in SEQ ID NO: 1 under stringent conditions and yet encodes a polypeptide having taurine transporter activity.

The novel polypeptides of the present invention are hamster taurine transporter and those polypeptides which are functionally equivalent thereto.

In the present invention, the expression "functionally equivalent to hamster taurine transporter" means having activities similar to the activities of hamster taurine transporter, such as taurine-binding activity, activity to transport taurine into cells, etc. Such a polypeptide encompasses, for example, mutants of hamster taurine transporter.

As methods well-known to those skilled in the art for preparing polypeptides functionally equivalent to a specific polypeptide, methods of introducing mutations into polypeptides may be given. For example, those skilled in the art could prepare polypeptides functionally equivalent to hamster taurine transporter by appropriately introducing mutations into amino acids of hamster taurine transporter by site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W. and Fritz H J (1987) Methods. Enzymol. 154, 350-367; Kunkel, T A (1985) Proc Natl Acad Sci USA. 82, 488-492; Kunkel (1988) Methods Enzymol. 85, 2763-2766). Mutations in amino acids may also occur in nature. Thus, a polypeptide which has an amino acid derived from the amino acid sequence of the hamster taurine transporter of the present invention by mutation of one or more amino acids and is functionally equivalent to hamster taurine transporter is also included in the polypeptide of the present invention.

Specific examples of polypeptides functionally equivalent to the hamster taurine transporter of the present invention include, but are not limited to, a polypeptide having an amino acid sequence derived from the amino acid sequence of the hamster taurine transporter by deletion of one or more amino acids, preferably 1-30 amino acids, more preferably 1-20 amino acids, even more preferably 1-10 amino acids, the most preferably 1-5 amino acids; a polypeptide having an amino acid sequence derived from the amino acid sequence of the hamster taurine transporter by addition of one or more amino acids, preferably 1-30 amino acids, more preferably 1-20 amino acids, even more preferably 1-10 amino acids, the most preferably 1-5 amino acids; and a polypeptide having an amino acid sequence derived from the amino acid sequence of the hamster taurine transporter by substitution of one or more amino acids, preferably 1-30 amino acids, more preferably 1-20 amino acids, even more preferably 1-10 amino acids, the most preferably 1-5 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, G, H, K, S and T), amino acids with an aliphatic side chain (G, A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

It has been reported that a polypeptide having an amino acid sequence derived from an original amino acid sequence by modification (such as deletion, addition and/or substitution of one or more amino acids) maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G et al., Proc. Natl. Acad. Sci. USA (1982) 79, 6409-6413).

As one example of the polypeptide in which one or more amino acid residues are added to the hamster taurine transporter of the present invention, a fusion polypeptide comprising the hamster taurine transporter may be given. Such a fusion polypeptide is composed of the protein of the invention (hamster taurine transporter) and other polypeptide fused thereto. Such a fusion polypeptide is included in the present invention. Such a fusion polypeptide may be prepared by linking a gene encoding the hamster taurine transporter of the present invention in frame with a gene encoding the other polypeptide, transferring the resultant DNA into an expression vector and expressing the DNA in a host cell. Techniques known to those skilled in the art may be used. There is no limitation on the polypeptide to be fused to the polypeptide of the present invention.

Examples of polypeptides to be fused to the polypeptide of the present invention include, but are not limited to, FLAG (Hopp, T. P. et al., BioTechnology (1988) 6, 1204-1210), 6×His comprising six histidine (His) residues, 10×His, influenza hemagglutinin (A), human c-myc fragment, VSV-GP fragment, p18HIV fragment, T7-tag, HSV-tag, E-tag, SV40T antigen fragment, lck tag, α-tubulin fragment, B-tag, protein C fragment, glutathione-S-transferase (GST), influenza hemagglutinin (HA), immunoglobulin constant region, β-galactosidase and maltose-binding protein (MBP).

A commercially available gene encoding such polypeptide is fused to the gene encoding the polypeptide of the present invention. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence of the hamster taurine transporter of the present invention based on that DNA sequence or a part thereof, and isolate polypeptides functionally equivalent to the hamster taurine transporter from that DNA. Thus, a polypeptide which is encoded by a DNA hybridizing to the DNA, or a part thereof, encoding the hamster taurine transporter of the present invention and is functionally equivalent to the hamster taurine transporter of the present invention is also included in the polypeptide of the present invention.

Hybridization conditions for isolating a DNA encoding a polypeptide functionally equivalent to the hamster taurine transporter of the present invention can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques usually has high homology with the hamster taurine transporter of the present invention in the amino acid sequence. The polypeptide of the present invention also include those polypeptides which are functionally equivalent to the hamster taurine transporter of the present invention and have high homology with the amino acid sequence of the hamster taurine transporter of the present invention. The term "high homology" refers to usually 97% or more homology, preferably 98% or more homology, more preferably 99% or more homology. For determination of the homology of polypeptides, the algorithm described in Wilbur, W J. and Lipman, D. J., Proc. Natl. Acad. Sci. USA (1983) 80, 726-730 may be followed.

The polypeptide of the present invention may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of the hamster taurine transporter of the present invention, the polypeptide is included in the present invention. For example, when the polypeptide of the present invention is expressed in a prokaryote (e.g., *Escherichia coli*), a methionine reside is added to the N-terminus of the initial amino acid sequence of the polypeptide. When the polypeptide of the present invention is expressed in a eukaryote (e.g., a mammalian cell), the N-terminal signal sequence is removed. The polypeptide of the present invention includes such polypeptides.

The polypeptide of the present invention may be prepared as a recombinant polypeptide or a natural polypeptide by methods known to those skilled in the art. A recombinant polypeptide may be prepared by incorporating a DNA encoding the polypeptide of the present invention in an appropriate expression vector, introducing the vector into an appropriate host cell, collecting the resultant transformant, extracting a crude polypeptide, and then purifying the polypeptide by chromatography (such as ion exchange, reversed phase or gel filtration chromatography, or affinity chromatography in which an antibody to the polypeptide of the present invention is fixed in a column) or a combination of these chromatographic techniques.

When the polypeptide of the present invention is expressed in a host cell (e.g., animal cell or *E. coli*) as a fusion polypeptide with glutathione-S-transferase polypeptide or as a recombinant polypeptide with histidine residues added thereto, the expressed polypeptide may be purified with a glutathione column or a nickel column.

After purification of a fusion polypeptide, regions other than the polypeptide of interest may be cut off by thrombin or factor Xa and removed from the fusion polypeptide.

When the polypeptide of the present invention is a natural polypeptide, the polypeptide may be isolated by purification methods known to those skilled in the art. For example, an extract from tissues or cells expressing the polypeptide of the present invention may be applied to an affinity column to which an antibody to the hamster taurine transporter described later is bound. The antibody may be either a polyclonal antibody or a monoclonal antibody.

Further, the present invention provides a DNA encoding a taurine transporter, which is any one of the following (a) to (e), provided that DNA having the nucleotide sequence as shown in SEQ ID NO: 3, DNA having the nucleotide sequence as shown in SEQ ID NO: 5, and DNA having the nucleotide sequence as shown in SEQ ID NO: 7 are excluded:

(a) a DNA encoding a polypeptide having the amino acid sequence as shown in SEQ ID NO: 2;
(b) a DNA encoding a polypeptide which has an amino acid sequence derived from the amino acid sequence as shown in SEQ ID NO: 2 by substitution, deletion, addition and/or insertion of one or more (several) amino acid residues and yet has taurine transporter activity;
(c) a DNA encoding a polypeptide having 97% or more amino acid sequence homology with the amino acid sequence as shown in SEQ ID NO: 2 and yet having taurine transporter activity;
(d) a DNA having the nucleotide sequence as shown in SEQ ID NO: 1; or
(e) a DNA which hybridizes to a DNA complementary to a DNA having the nucleotide sequence as shown in SEQ ID NO: 1 under stringent conditions and yet encodes a polypeptide having taurine transporter activity.

The DNA of the present invention is used in the in vivo or in vitro production of the polypeptide of the present invention as described above. Further, the DNA of the present invention may be used in the creation of a cell which strongly expresses the hamster taurine transporter. The DNA of the present invention may take any form as long as it is capable of encoding the polypeptide of the present invention. That is, the DNA may be, for example, a cDNA synthesized from mRNA, a genomic DNA or a chemically synthesized DNA. It should be noted that, as long as the DNA is capable of encoding the polypeptide of the present invention, the DNA may have any nucleotide sequence based on the degeneracy of genetic codes.

The DNA of the present invention may be prepared by methods known to those skilled in the art. For example, the DNA may be prepared by preparing a cDNA library from a cell expressing the polypeptide of the present invention and performing hybridization using a part of the DNA sequence of the present invention (e.g., SEQ ID NO: 1) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA of the present invention by preparing RNA from a cell expressing the polypeptide of the present invention, synthesizing oligo DNA molecules based on the DNA sequence of the present invention (e.g., SEQ ID NO: 1), and performing PCR using the oligo DNA molecules as primers to thereby amplify a cDNA encoding the taurine transporter.

Further, by determining the nucleotide sequence of the resultant cDNA, it is possible to determine the translation region encoding the polypeptide and to obtain the amino acid sequence of the polypeptide of the present invention. Further, by screening a genomic library using the resultant cDNA as a probe, it is possible to isolate a genomic DNA.

Specifically, the following procedures may be used. First, mRNA is isolated from cells, tissues or the like expressing the polypeptide of the present invention. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., E. coli), followed by selection of resultant colonies to thereby obtain a desired recombinant vector. The nucleotide sequence of the DNA of interest may be confirmed by a known method such as the dideoxynucleotide chain termination method.

Further, a nucleotide sequence of a higher expression efficiency can be designed for the DNA of the present invention by considering the frequency of codon usage in the host to be used for expression (Grantham, R. et al., Nucleic Acids Research (1981) 9, p. 43-74). Further, the DNA of the present invention can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA of the present invention also includes a DNA which hybridizes to a DNA having the nucleotide sequence as shown in SEQ ID NO: 1 under stringent conditions and encodes a polypeptide functionally equivalent to the hamster taurine transporter.

Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding the hamster taurine transporter of the present invention. The DNA of the present invention also includes a DNA which encodes a polypeptide functionally equivalent to the hamster taurine transporter of the present invention and has high identity with a DNA encoding the hamster taurine transporter of the present invention. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score =100 and wordlength=12, for example. Specific procedures for these analysis methods are known, for example, as provided by the National Center for Biotechnology Information's website.

Further, the present invention provides a vector into which the DNA of the present invention has been inserted. The vector of the present invention is useful for retaining the DNA of the present invention within the host cell and for permitting expression of the polypeptide of the present invention (i.e., hamster taurine transporter or a polypeptide functionally equivalent thereto). The vector of the present invention is also useful for permitting the host cell to strongly express the taurine transporter. By permitting the host cell to strongly express the taurine transporter, taurine uptake into the host cell is promoted, which leads to an increased production of a desired polypeptide in the host cell.

When the host cell to be used is E. coli, it is preferable that the vector has a replication origin ("ori") so that the vector is largely amplified in E. coli (e.g., JM109, DH5α, HB101 and XL1-Blue) and prepared in large quantity, and also genes for selecting transformed E. coli (e.g., drug resistance genes that enable discrimination of transformant with some drugs such as ampicillin, tetracycline, kanamycin or chloramphenicol). Examples of preferable vectors include, but are not limited to, M13 vectors, pUC vectors, pBR322, pBluescript and pCR-Script. In addition to these vectors, pGEM-T, pDIRECT, pT7, etc. may be enumerated when the vector is used for the purpose of subcloning a cDNA and cutting off the subcloned cDNA. When the vector is used for the purpose of producing the polypeptide of the present invention, an expression vector is especially useful. When expression in E. coli is intended, the expression vector preferably has the above-described features so that the vector is amplified in E. coli, and it also preferably has a promoter which allows efficient expression in E. coli such as JM109, DH5α, HB101 or XL1-Blue, e.g., lacZ promoter (Ward et al, Nature (1989) 341, 544-546; FASEB J. (1992) 6, 2422-2427), araB promoter (Better et al, Science (1988) 240, 1041-1043) or T7 promoter. Specific examples of such vector include, in addition to those listed above, pGEX-5X-1 (Pharmacia), QIAexpress system (Qiagen), pEGFP, or pET (for its host, T7 RNA polymerase-expressing BL21 is preferred).

The vector may comprise signal sequences for polypeptide secretion. When the polypeptide is to be produced in the periplasm of *E. coli*, pelB signal sequence (Lei, S. P. et al., J. Bacteriol. (1987) 169, 4379) may be used as a signal sequence for polypeptide secretion. Introduction of the vector into a host cell may be performed, for example, by the calcium chloride method or electroporation.

In cases where a host cell other than *E. coli* is used, vectors useful for producing the polypeptide of the present invention include, but are not limited to, mammal-derived expression vectors [e.g., pcDNA3 from Invitrogen; pEGF-BOS (Nucleic Acids. Res. 1990, 18(17), p. 5322); pEF, pCDM8], insect cell-derived expression vectors (e.g., Bac-to-BAC baculovairus expression system from GIBCO BRL; pBacPAK8), plant-derived expression vectors (e.g., pMH1, pMH2), animal virus-derived expression vectors (e.g., pHSV, pMV, pAdex-Lcw), retrovirus-derived expression vectors (e.g., pZIpneo), yeast-derived expression vectors (e.g., *Pichia* Expression Kit fron Invitrogen; pNV11; SP-Q01), and *Bacillus subtilis*-derived expression vectors (e.g., pPL608, pKTH50).

When expression of the polypeptide in animal cells (such as CHO cells, COS cells, NIH3T3 cells, etc.) is intended, the vector preferably has a promoter necessary for expressing the polypeptide in those cells. Examples of such promoter include, but are not limited to, SV40 promoter (Mulligan et al, Nature (1979) 277, 108), MMLV-LTR promoter, EF1α promoter (Mizushima et al., Nucleic Acids Res. (1990) 18, 5322) and CMV promoter. More preferably, the vector also has genes for selecting transformed cells (e.g., drug resistance genes that enable discrimination with drugs such as neomycin or G418). Examples of vectors having such properties include, but are not limited to, pMAM, pDR2, pBK-RSV, PBK-CMY, pOPRSV and pOP13.

Further, when stable expression of a gene of interest and intracellular amplification of the copy number of the gene are indented, the following method may be used. Briefly, into CHO cells lacking a nucleic acid synthesis pathway, a vector having DHFR gene that complements the lack (e.g., pCHOI) is introduced, followed by amplification with methotrexate (MTX). On the other hand, when tentative expression of a gene of interest is intended, a method may be used in which COS cells carrying a gene expressing SV40T antigen on the chromosome is transformed with a vector having the replication origin of SV40 (e.g., pcD). As the replication origin, a replication origin derived from polyomavirus, adenovirus or bovine papillomavirus (BPV) may also be used. Further, the expression vector may contain selectable markers for amplifying the copy number of the gene in a host cell system. Examples of such selectable markers include, but are not limited to, aminoglycoside phosphotransferase (APH) gene, thymidine kinase (TK) gene, *E. coli* xanthine-guanine phosphoribosyl transferase (Ecogpt) gene and dihydrofolate reductase (dhfr) gene.

The present invention also provides a host cell into which the vector of the present invention has been transferred. The host cell into which the vector of the present invention is transferred is not particularly limited. For example, *E. coli* or various animal cells may be used. The host cell of the present invention may be used, for example, as a production system for the preparation or expression of the polypeptide of the present invention. Further, the host cell of the present invention is capable of expressing the taurine transporter strongly, promoting taurine uptake, and increasing the yield of the desired polypeptide. For the production of the polypeptide, there are in vivo and in vitro production systems. Examples of in vitro production systems include systems using eukaryotes and systems using prokaryotes.

When eukaryotes are used, animal cells, plant cells, fungal cells, etc. may be used as the host. Specific examples of animal cells include mammalian cells, such as CHO cells (J. Exp. Med. (1995) 108, 945), COS cells, 3T3 cells, myeloma cells, BHK (baby hamster kidney) cells, HeLa cells and Vero cells; amphibian cells, such as oocytes of *Xenopus laevis* (Valle, et al., Nature (1981) 291, 358-340); or insect cells, such as sf9, sf21 and Tn5 cells. Amoung CHO cells, dhfr-CHO lacking DHFR gene (Proc. Natl. Acad. Sci. USA (1980) 77, 4216-4420) and CHO K-1 (Proc. Natl. Acad. Sci. USA (1968) 60, 1275) are used with particular advantage. When high expression is intended in an animal cell, CHO cells are especially preferred. Introduction of the expression vector into the host cell may be performed by such methods as the calcium phosphate method, the DEAE dextran method, a method using a cationic ribosome DOTAP (Boehringer-Mannheim), electroporation, lipofection, etc.

As plant cells for polypeptide production, a *Nicotiana tabacum*-derived cell is known as a polypeptide production system and this may be subjected to callus culture. As fungal cells for polypeptide production, specific examples include yeast belonging to the genus *Saccharomyces*, e.g., *Saccharomyces cerevisiae*, and filamentous fungi belonging to the genus *Aspergillus*, e.g., *Aspergillus niger*.

When prokaryotes are used, production systems using bacterial cells are known. Specific examples of such bacterial cells include *E. coli* (such as JM109, DH5α, HB101) and *Bacillus subtilis*.

The polypeptide encoded by a gene of interest may be obtained by transforming these cells with the gene of interest and culturing the transformed cells in vitro. The culture may be performed by known methods. For example, as a culture broth for animal cells, a medium such as DMEM, MEM, RPMI1640 or IMDM may be used. A serum supplement such as fetal calf serum (FCS) may be used jointly. Alternatively, serum-free culture may be performed. The pH during culture is preferably about 6 to 8. The culture is usually performed at about 30-40° C. for about 15-200 hours. If necessary, replacement of the medium, aeration and agitation are carried out.

On the other hand, in vivo production systems include those using animals or plants. A gene of interest is transferred into these animals or plants to produce the polypeptide in the animal bodies or plant bodies. Then, the polypeptide is collected. The term "host" as used herein includes such animals or plants.

When animals are used, available production systems include those using mammals or insects. Goat, pig, sheep, mouse and cattle may be used as mammals (Vicki Glaser, SPECTRUM Biotechnology Applications, 1993). When mammals are used, transgenic animals may be used.

First, a gene of interest is fused to a gene encoding a polypeptide produced inherently in milk (such as goat 0-casein) to thereby prepare a fusion gene. A DNA fragment containing this fusion gene is injected into a goat embryo, which is then implanted in the uterus of a female goat. The polypeptide of interest can be obtained from the milk produced by transgenic goats born from the goat which accepted the embryo or the offspring of the transgenic goats. In order to increase the yield of milk containing the polypeptide produced by the transgenic goats, hormones may be appropriately administered to the transgenic goats (Ebert, K. M. et al., Bio/Technology (1994) 12, 699-702).

Examples of insects which may be used include silkworm. In this case, silkworm is infected with baculovirus carrying a transferred gene encoding the polypeptide of interest. The polypeptide of interest can be obtained from the body fluid of the silkworm (Susumu, M. et al., Nature (1985) 315, 592-594).

Furthermore, when plants are used, tobacco can typically be used. When tobacco is used, a gene encoding the polypeptide of interest is inserted into a plant expression vector (e.g., pMON 530), which is then transferred into a bacterium such as *Agrobacterium tumefaciens*. A tobacco plant (e.g., *Nicotiana tabacum*) is infected with the resultant bacterium. The polypeptide of interest can be obtained from leaves of this plant (Julian, K.-C. Ma et al., Eur. J. Immunol. (1994) 24, 131-138).

The polypeptide thus obtained can be isolated from the inside of the host cell or from its outside (e.g., medium), and purified to a substantially pure and homogeneous polypeptide. Isolation and purification of polypeptides can be performed using conventional isolation and purification methods for polypeptides, and are not limited in any way. For example, polypeptides can be isolated and purified by appropriate selection and combination of various tools and techniques, such as chromatography columns, filters, ultrafiltration, salting-out, precipitation with solvent, extraction with solvent, distillation, immunoprecipitation, SDS-polyacrylamide gel electrophoresis, isoelectric focusing, dialysis, recrystallization, etc.

Examples of chromatography include affinity chromatography, ion exchange chromatography, hydrophobic chromatography, gel filtration, reverse-phase chromatography, adsorption chromatography, etc. (Strategies for Protein Purification and Characterization: A Laboratory Course Manual. Ed. Daniel R. Marshak et al., Cold Spring Harbor Laboratory Press, 1996). These chromatographic techniques can be carried out using liquid phase chromatography, for example, HPLC, FPLC, etc. The present invention also includes those polypeptides highly purified using these purification methods.

Before or after the purification, it is also possible to give optional modifications to the polypeptide or remove a partial peptide therefrom by reacting the polypeptide with an appropriate polypeptide modification enzyme. Examples of such enzyme include, but are not limited to, trypsin, chymotrypsin, lysyl endopeptidase, protein kinase and glucosidase.

The present invention also provides an antibody that binds to the polypeptide of the present invention. The form of the antibody of the present invention is not particularly limited; the antibody of the present invention includes polyclonal antibodies and monoclonal antibodies. In addition, antisera obtained by immunizing immune animals such as rabbit with the polypeptide of the present invention, and polyclonal antibodies and monoclonal antibodies of every class are also included in the antibody of the present invention.

The polypeptide used as a sensitizing antigen may be an intact polypeptide or a partial peptide thereof. Examples of such partial peptides include amino (N)-terminal fragments and carboxyl (C)-terminal fragments of the polypeptide. The term "antibody" as used herein means an antibody that reacts with the full length polypeptide or fragments thereof.

After inserting a gene encoding the polypeptide of the present invention or a fragment thereof into a known expression vector and transforming the host cell described earlier in this specification with this expression vector, the desired polypeptide or a fragment thereof is obtained from inside and outside of the host cells by a known method. This polypeptide or a fragment thereof may be used as a sensitizing antigen.

Alternatively, cells expressing the polypeptide of the present invention or a lysate thereof, or a chemically synthesized polypeptide of the present invention may also be used as a sensitizing antigen.

Although there is no particular limitation on the species of mammals to be immunized with a sensitizing antigen, it is preferable to select mammals taking into consideration the compatibility with the parent cell to be used for cell fusion, and animals of the rodent, lagomorph and primate are generally used.

For example, mouse, rat, hamster and the like are used as rodent animals; rabbit is used as a lagomorphic animal, and monkey is used as a primate animal. Among monkeys, catarrhine monkeys (old world monkeys) are used, as exemplified by cynomolgus monkey (*Macaca fascicularis*), rhesus monkey, baboon, chimpanzee and the like.

Immunization of animals with a sensitizing antigen is carried out according to any known method. Generally, immunization is performed by intraperitoneal or subcutaneous injection of the antigen to mammals. Specifically, the antigen is appropriately diluted and suspended in PBS (Phosphate-Buffered Saline), physiological saline or the like, optionally mixed with a suitable amount of usual adjuvant (e.g., Freund's complete adjuvant), emulsified and then administered to mammals, preferably followed by several booster injections of the antigen mixed with an appropriate amount of Freund's incomplete adjuvant every 4 to 21 days. In addition, suitable carriers can be used at the time of immunization with the antigen. Subsequently, elevation of the level of a desired antibody in the sera of animals is confirmed by a conventional method.

In order to obtain polyclonal antibodies to the polypeptide of the present invention, the blood of mammals sensitized with the antigen is withdrawn after confirming elevation of the level of a desired antibody in sera. Then, sera are isolated from the blood by a known method. A serum containing a polyclonal antibody may be used as the polyclonal antibody. If necessary, a fraction containing the polyclonal antibody may be further isolated from the serum and used as the polyclonal antibody. For example, a fraction recognizing only the polypeptide of the present invention is obtained by using an affinity column to which the polypeptide of the present invention has been coupled, and further purified by using protein A or protein G column to prepare immunoglobulin G or M.

Monoclonal antibodies can be obtained by removing immunocytes from the mammals sensitized with the above-described antigen, after confirming the elevation of the level of a desired antibody in their sera, and then subjecting the immunocytes to cell fusion. Immunocytes preferably used for cell fusion are spleen cells. Parent cells to be fused to the above-described immunocytes are preferably mammalian myeloma cells, more preferably myeloma cells which have acquired characteristics for the selection of fused cells with drugs.

Cell fusion between the above-described immunocytes and myeloma cells can be carried out according to a known method, for example, the method of Milstein et al. (Galfre, G. and Milstein, C., Methods Enzymol. (1981) 73, 346).

Hybridomas thus obtained by cell fusion are selected by culturing them in a conventional selection medium, for example, HAT culture medium (culture broth containing hypoxanthine, aminopterin and thymidine). Culturing in the HAT medium is continued for a sufficient time to kill other cells (non-fused cells) than desired hybridomas, usually for several days to several weeks. Then, conventional limiting culture-dilution method is performed to carry out screening and cloning of hybridomas producing the antibody of interest.

Subsequently, the resultant hybridomas are transplanted into the abdominal cavities of mice, and abdominal dropsies are collected from the mice to thereby obtain monoclonal antibodies. These monoclonal antibodies may be purified by ammonium sulfate precipitation, with protein A or protein G column, by DEAE ion exchange chromatography, with affinity column to which the polypeptide of the present invention has been coupled, etc. The antibody of the present invention can be used for purification and detection of the polypeptide of the present invention.

Further, the thus obtained monoclonal antibodies can also be prepared as recombinant antibodies using recombinant DNA techniques (see, for example, Borrebaeck, C. A. K. and Larrick J. W., THERAPEUTIC MONOCLONAL ANTIBODIES, Published in the United Kingdom by MACMILLAN PUBLISHERS LTD, 1990). A recombinant antibody is produced by cloning a gene encoding the recombinant antibody from hybridomas or the antibody-producing immunocytes (such as sensitized lymphocytes), incorporating the gene into an appropriate vector, and transferring the vector into host cells for antibody production. The produced recombinant antibody is also included in the present invention.

The antibody of the present invention may be antibody fragments or modified antibodies as long as they are capable of binding to the polypeptide of the present invention. Examples of such antibody fragments include Fab, F(ab')2, Fv, or a single-chain Fv (scFv) prepared by linking the Fv of H-chain to the Fv of L-chain via a suitable linker (Huston, J. S. et al., Proc. Natl. Acad. Sci. USA (1988) 85, 5879-5883). Specifically, antibody fragments are produced by digesting the antibody with enzymes, for example, papain or pepsin; or by constructing a gene encoding such a fragment, inserting the gene into an expression vector, and expressing it in a suitable host cell (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enymol. (1986) 121, 652-663; Rousseaux, J. et al., Methods Enzymol. (1986) 121, 663-669; Bird, R. E. and Walker, B. W., Trends Biotechnol. (1991) 9, 132-137).

As a modified antibody, the antibody bound to various molecules such as polyethylene glycol (PEG) may be also used. The "antibody" of present invention also includes these modified antibodies. These modified antibodies can be prepared by chemically modifying the antibody obtained as described above. These modification methods have been already established in the art.

Antibodies obtained as described above can be purified to homogeneity. For the isolation and purification of the antibody used in present invention, any methods of isolation and purification used for conventional polypeptides may be used. For example, chromatography columns such as affinity chromatography columns, filters, ultrafiltration, salting-out, dialysis, SDS-polyacrylamide gel electrophoresis, isoelectric focusing, etc. may be used independently or in appropriate combinations (Antibodies: A Laboratory Manual. Ed Harlow and David Lane, Cold Spring Harbor Laboratory, 1988) but these are not the sole examples. Concentration of the antibody obtained as described above can be determined by measuring absorbance or by a method such as enzyme-linked immunosorbent assay (ELISA).

Examples of columns used in affinity chromatography include protein A column and protein G column. As columns using protein A, Hyper D, POROS, Sepharose F F. (Pharmacia), etc. may be given.

Examples of chromatography other than affinity chromatography include ion exchange chromatography, hydrophobic chromatography, gel filtration, reversed-phase chromatography, adsorption chromatography, etc. (Strategies for Protein Purification and Characterization: A Laboratory Course Manual. Ed Daniel R. Marshak et al., Cold Spring Harbor Laboratory Press, 1996). These chromatographic techniques can be carried out using liquid phase chromatography such as HPLC, FPLC, etc.

Furthermore, absorbance measurement, ELISA, EIA (enzyme immunoassay), RIA (radioimmunoassay) or fluorescent antibody technique can be used as methods for measuring the antigen-binding activity of the antibody of present invention. When ELISA is used, the polypeptide of the present invention is added to plates on which the antibody of the present invention has been immobilized, and then a sample containing an antibody of interest (e.g., culture supernatant of antibody-producing cells or purified antibody) is added to the plates. A secondary antibody labeled with an enzyme (e.g., alkaline phosphatase) that recognizes the antibody is added to the plates. After incubating and washing the plates, a substrate for the enzyme (e.g., p-nitrophenyl phosphate) is added to determine the absorbance to thereby evaluate the antigen-binding activity. Instead of the entire polypeptide, a fragment thereof may be used. For example, fragments comprising its C-terminal or N-terminal may be used. For evaluating the activity of the antibody of the present invention, BIAcore (Pharmacia) may be used.

EXAMPLES

Hereinbelow, the present invention will be described in more detail with reference to the following Examples. It should be noted that these Examples are provided only for illustrating the present invention and not for limiting the scope of the present invention.

Example 1

Cloning of CHO Cell-Derived Hamster Taurine Transporter Gene

Figure 1:
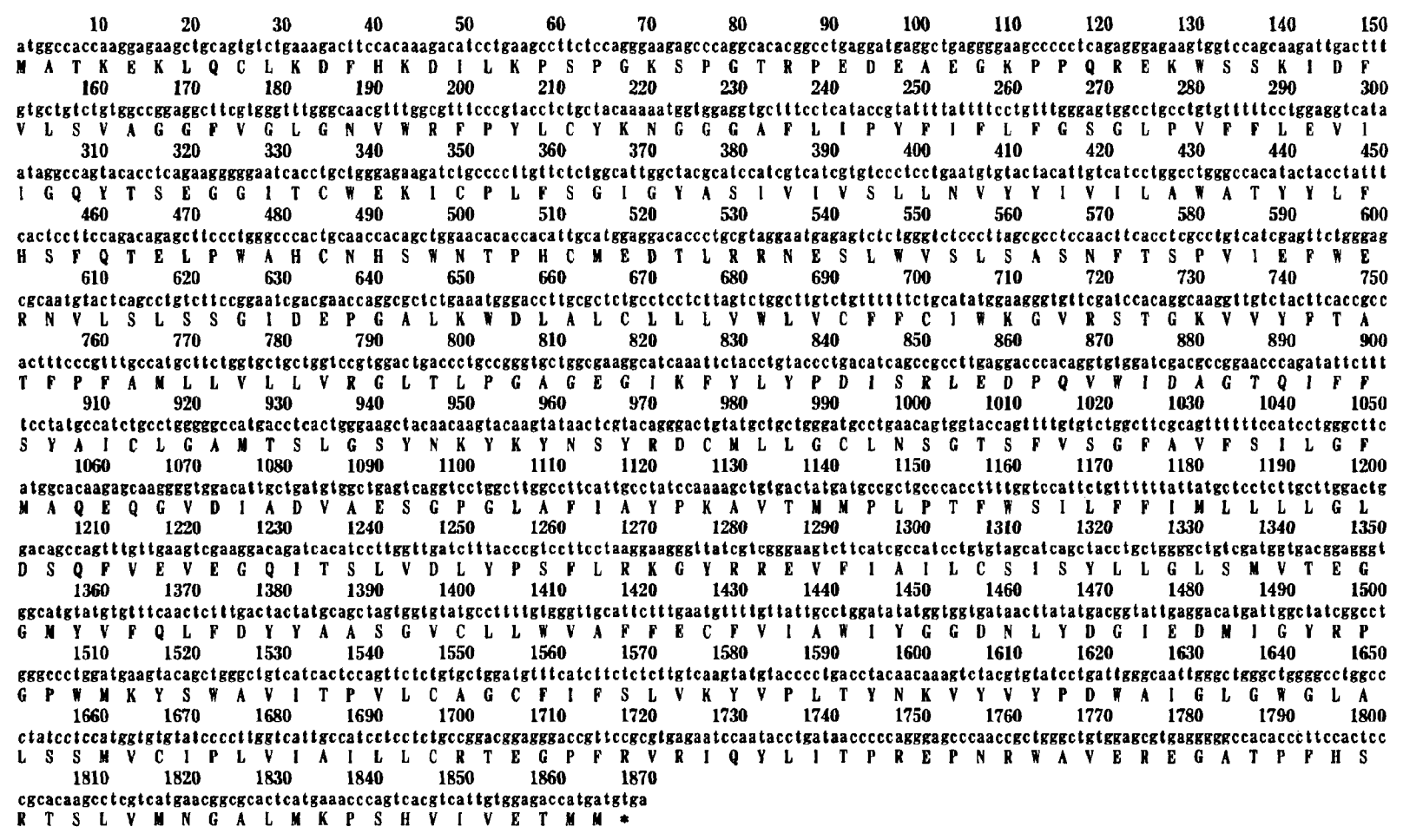

Total RNA was extracted from anti-IL-6 receptor antibody-producing cells (A CHO DXB11 cell line into which an anti-IL-6 receptor antibody gene had been transferred) (Japanese Unexamined Patent Publication No. Hei 8-99902), and then cDNA was synthesized therefrom in a poly(A) dependent manner. Hamster taurine transporter (TauT) gene was obtained by PCR using as a template the cDNA fragmented with three restriction enzymes, SalI, XhoI and EcoRI. As PCR primers, those containing the 5'-end and the 3'-end sequence conserved between rat and mouse TauTs were designed. The nucleotide sequence of the cloned gene was determined. From its homology with other TauT genes of known species, the cloned gene was confirmed to encode hamster TauT (FIG. 1). The amino acid sequence of hamster TauT has high homology with mouse TauT (96% identity), rat TauT (96% identity) and human TauT (93% identity); it was predicted that hamster TauT is a transporter with 12 transmembrane regions (FIG. 2).

Example 2

Figure 3:
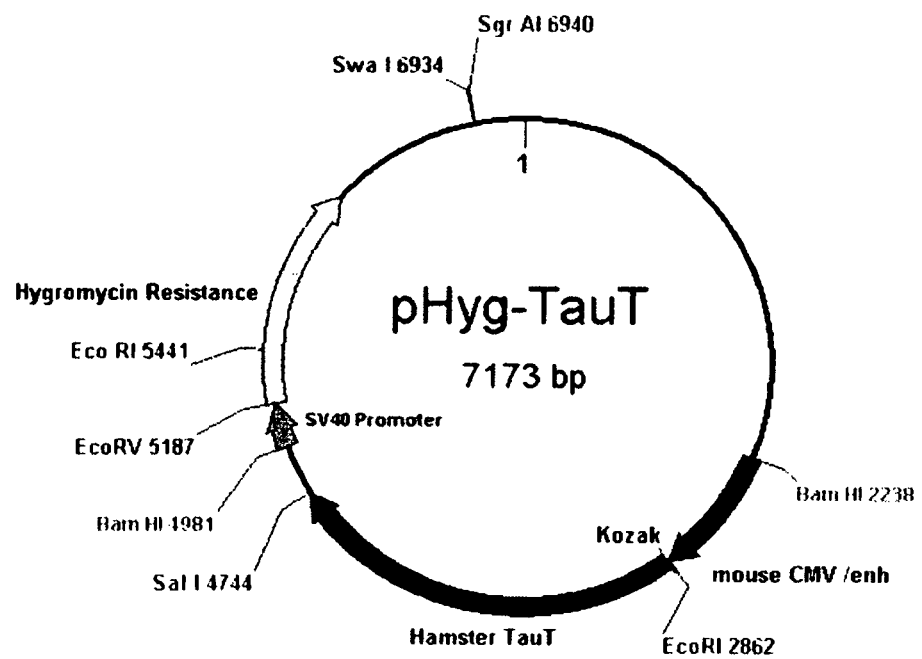
FIG. 3 shows a plasmid which was used for expressing hamster TauT (622 amino acids).
Figure 4:
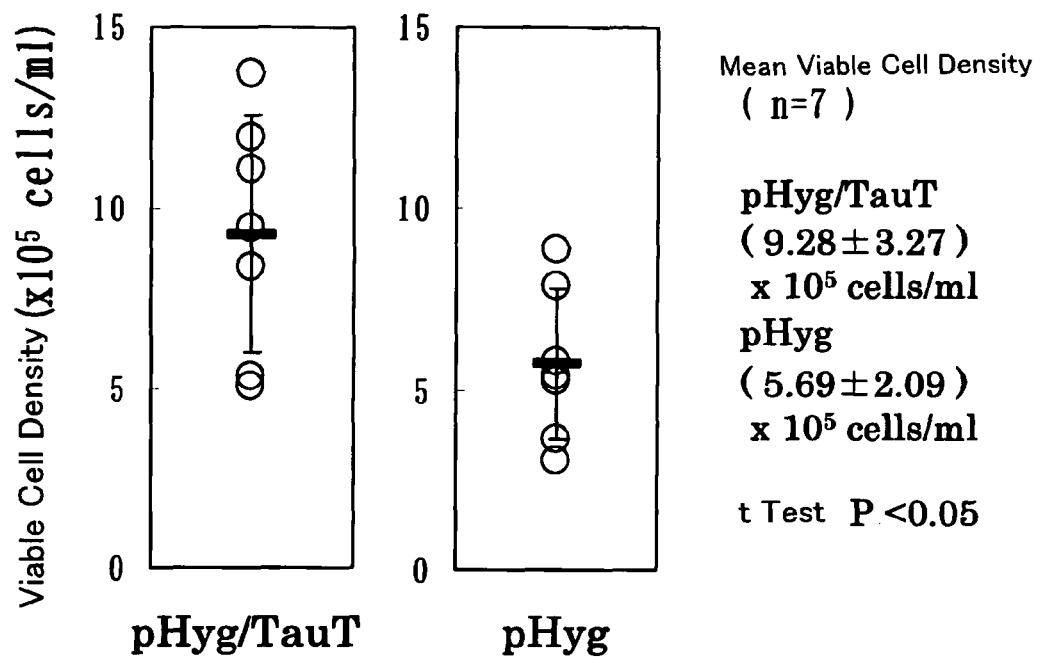
FIG. 4 shows viable cell density plots on day 7 of 50 ml shaker flask batch culture (n=7). The viable cell density in pHyg/TauT-transferred cell was superior to that in pHyg-transferred cell (P<0.05).
Figure 5:
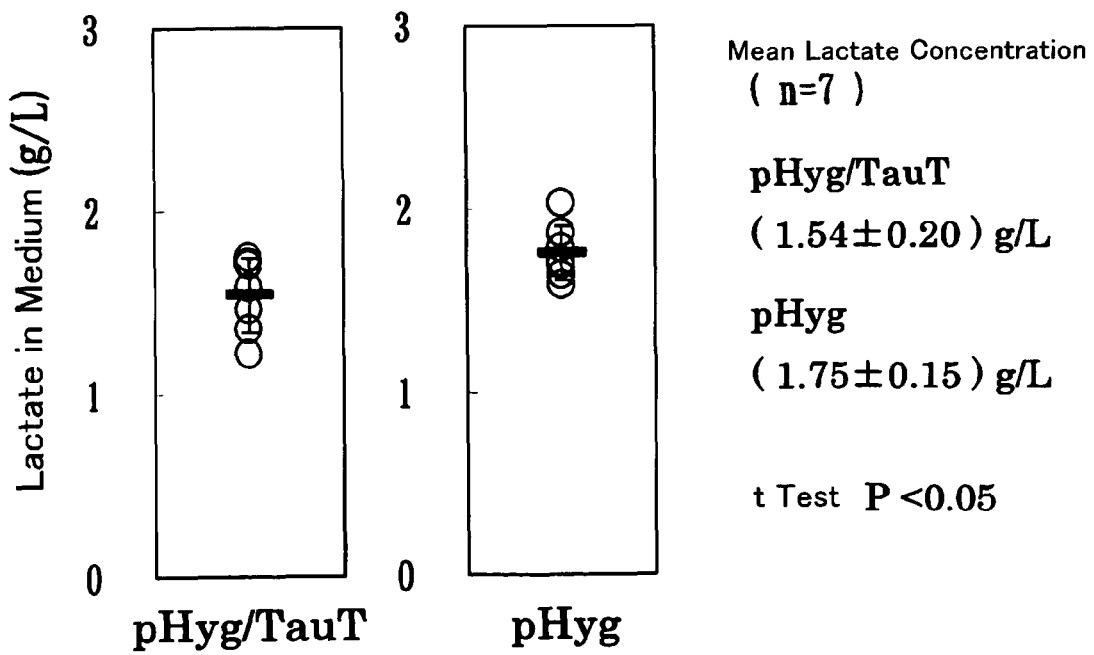
FIG. 5 shows lactate yield plots on day 7 of 50 ml shaker flask batch culture (n=7). pHyg/TauT-transferred cell produced less lactate, and was superior to pHyg-transferred cell (P<0.05).
Figure 6:
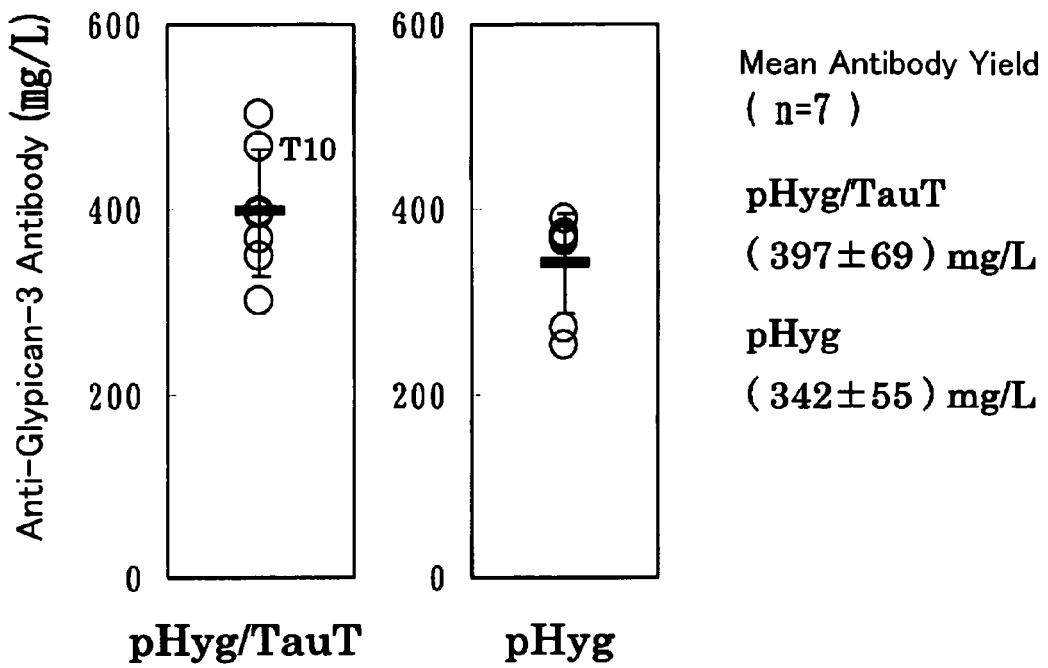
FIG. 6 shows anti-glypican-3 antibody yield plots on day 7 of 50 ml shaker flask batch culture (n=7). Four out of the 7 strains of pHyg/TauT-transferred cell showed antibody yields higher than the highest yield in pHyg-transferred cell.
Figure 7:
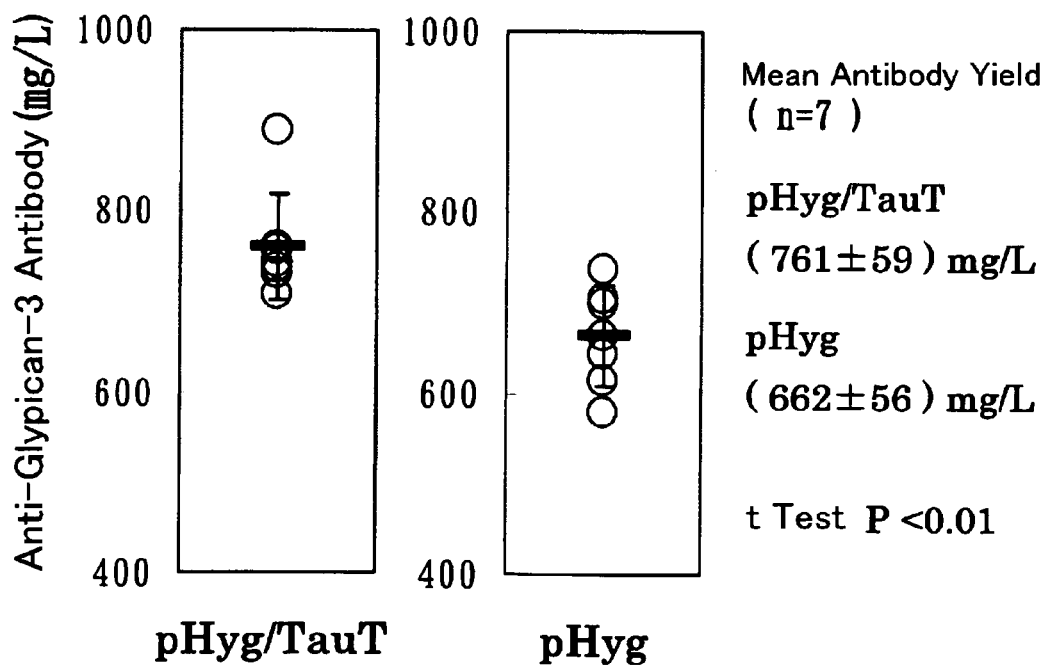
FIG. 7 shows anti-glypican-3 antibody yield plots on day 7 of 50 ml shaker flask fed-batch culture (n=7). The antibody yield in pHyg/TauT-transferred cell was superior to that in pHyg-transferred cell (P<0.01).
Figure 8:
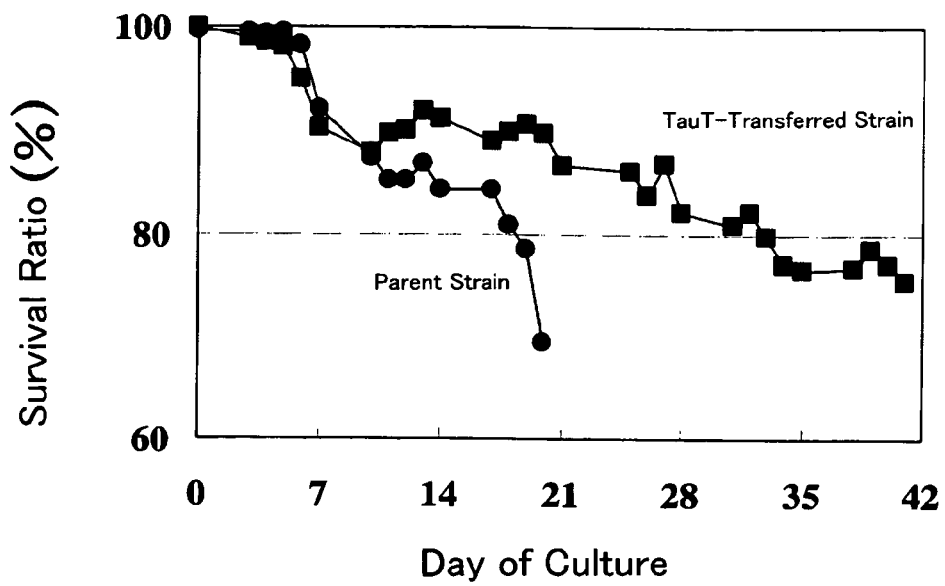
FIG. 8 is a graph showing the survival ratio of a pHyg/TauT-transferred cell T10 (which showed high growth ability during the expansion process in static culture) in 1 L jar fed-batch culture. The survival ratio of T10 was 80% or more even on day 32 of the culture. On the other hand, the survival ratio of the parent strain became less than 80% on day 19.
Figure 9:
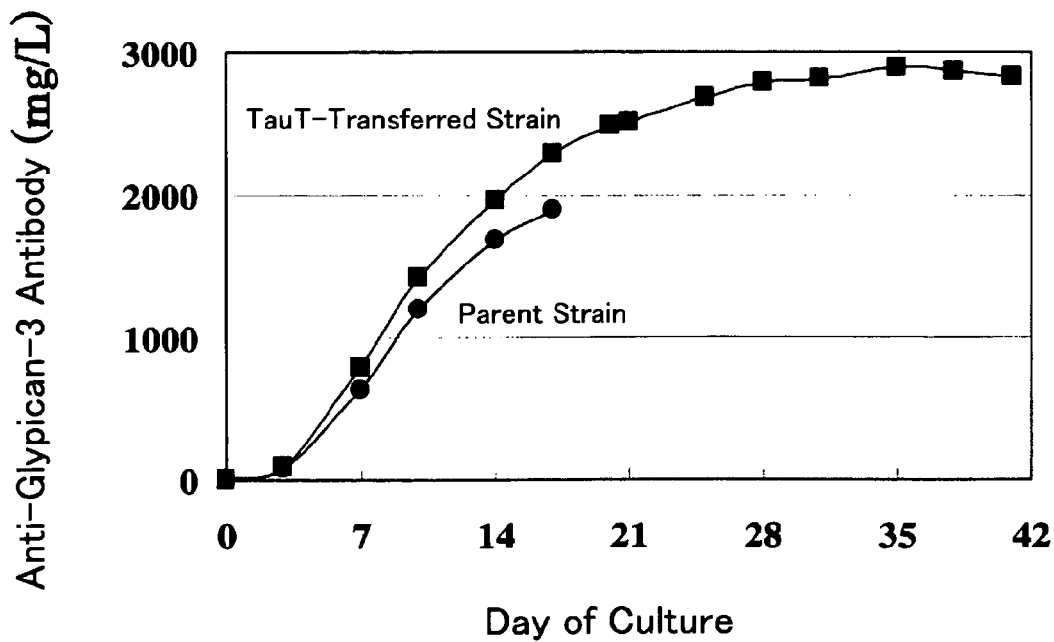
FIG. 9 is a graph showing the antibody yield of a pHyg/TauT-transferred cell T10 (which showed high growth ability during the expansion process in static culture) in 1 L jar fed-batch culture. The anti-glypican-3 antibody yield of T10 was 2.9 g/l on day 35 of the culture.
Figure 10:
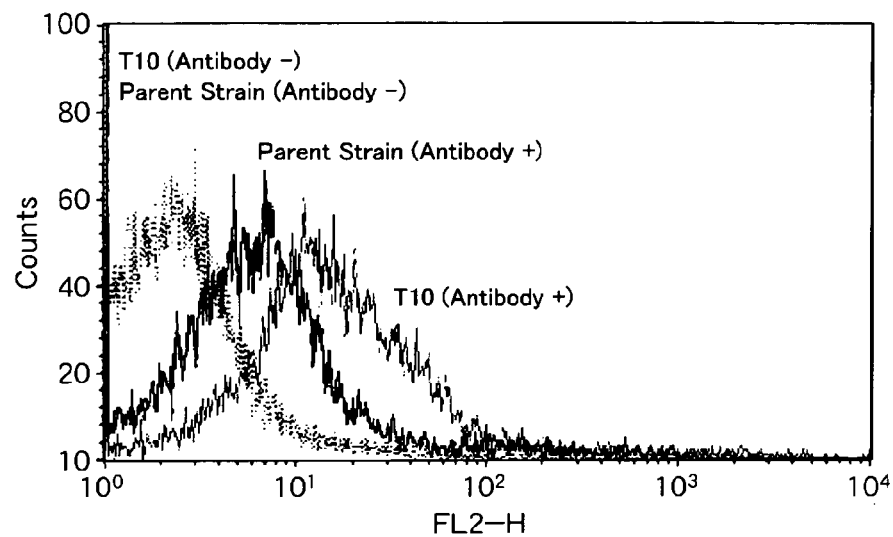
FIG. 10 shows the results of flow cytometric analysis indicating that TauT-transferred T10 cell is expressing TauT molecules on its cell membrane. As a primary antibody, rabbit anti-rat taurine transporter antibody (Alpha Diagnostics, US) was used (antibody ±). As a secondary antibody, donkey anti-rabbit IgG antibody-Pycoerythrin-conjugate (Abcam, UK) was used for labelling.

Increase in Viable Cell Density, Inhibition of Lactate Production and Increase in Antibody Yield, as Caused by Transfer of Hamster Taurine Transporter CMV promoter expression plasmid pHyg/TauT (FIG. 3) was constructed by adding Kozak sequence to the hamster TauT (hereinafter, TauT) gene obtained by cloning in Example 1. Control plasmid pHyg without pHyg/TauT or TauT gene was introduced by electroporation into the parent strain anti-glypican-3 antibody producing CHO cell (see WO 2006/006693). After selection of expression plasmid-transferred cells in the presence of hygromycin (400 μg/ml), all of the stably growing cell strains were expanded (pHyg/TauT: 8 strains; pHyg: 7 strains). TauT mRNA was prepared. Subsequently, 7 strains were confirmed to express TauT more strongly than the parent strain by the TaqMan method; they were selected as pHyg/TauT transferred cells. The mean mRNA expression level of these transferred cells (7 strains) was about 40 times larger than the control (7 strains). Cells of the total 14 strains were subjected to batch culture and fed-batch culture in 50 ml shaker flasks with an initial cell density of $2 \times 10^5$ cells/ml. On day 7 of culture (late-stage), viable cell densities, lactate yields and anti-glypican-3 antibody yields in those strains were compared. In batch culture, growth inhibitory substances such as lactate accumulate in culture broth as cells grow and their growth is inhibited. However, the viable cell densities (FIG. 4) and lactate yields (FIG. 5) in pHyg/TauT transferred cells were superior to those in pHyg transferred cells (t test; p<0.05). With respect to anti-glypican-3 antibody yield, 4 out of the 7 strains of pHyg/TauT-transferred cell showed antibody yields higher than the highest yield in pHyg-transferred cell (FIG. 6). Further, since superiority of pHyg/TauT transferred cells in anti-glypican-3 antibody yield became more evident (t test; P<0.01; FIG. 7) in fed-batch culture, pHyg/TauT transferred T10 strain (which showed the highest growth ability among the above 4 strains) and the parent strain were subjected to fed-batch culture in 1 L jar. As a result, the viable ratio of T10 was maintained at 80% or more even on day 32 of culture (FIG. 8), with inhibited lactate production. Consequently, its anti-glypican-3 antibody yield achieved 2.9 g/L on day 35 of culture (FIG. 9). It was confirmed by flow cytometric analysis that TauT-transferred T10 cell was expressing TauT molecules on the cell membrane (FIG. 10). These results suggest that by artificially expressing hamster Taut, it is possible to raise the potential of antibody-producing cells and create strains capable of enhanced antibody production.

Example 3

Inhibition of Ammonia Production, Taurine Uptake, Increase in Glutamine Consumption and Taurine Non-Dependent Antibody Yield in Hamster TauT Transferred Strains The parent strain and pHyg/TauT transferred strain were fed-batch cultured in 1 L jar with an initial cell density of $2 \times 10^5$ cells/ml. A part of the culture broth containing $450 \times 10^5$ cells was taken from the jar at appropriate time points. After the culture supernatant was separated by centrifugation, 1 ml of cooled sterile water containing a protease inhibitor (Complete Mini; Roche Diagnostics; Protease inhibitor cocktail tablets) was added to the cell pellet. Then, the cells were completely disrupted on ice in a sonicator (MISONIX ASTRASON MODEL XL2020) with a set of 5 seconds pulse-on and 5 seconds pulse-off being repeated 12 times. The total volume of the thus treated cells was applied to a centrifugal filter unit to thereby prepare a filtrate with a molecular weight of 5000 or less. This filtrate was used as a sample for determining intracellular amino acids. Each sample was subjected to detection and comparison of absorbance at 570 nm using a ninhydrin reagent L-8500 set (Wako PureChemical Industries) and an improved model of Hitachi fully automated amino acid analyzer (L-8500). Thus, various amino acid concentrations in samples were determined. Since the concentrations of amino acids and ammonia in culture broth were directly measured values, concentration comparisons in the order of μM were performed. On the other hand, since intracellular concentrations were obtained after addition of 1 ml of cooled sterile water to the cell pellet and sonication thereof, the measured concentrations of various amino acids and ammonia were converted into values per cell, followed by comparison of the converted values. To determine the ammonia concentration ratios shown in FIG. 11, the detected ammonia value per $450 \times 10^5$ cells in the parent strain at the start of 1 L jar fed-batch culture was taken as 1 and compared with detected values at the start of the culture and on days 6, 12 and 18 of the culture in the transferred strain. The taurine values in FIG. 12 and the glutamine values in FIG. 13 were also determined by the above-described amino acid analysis.

Figure 11:
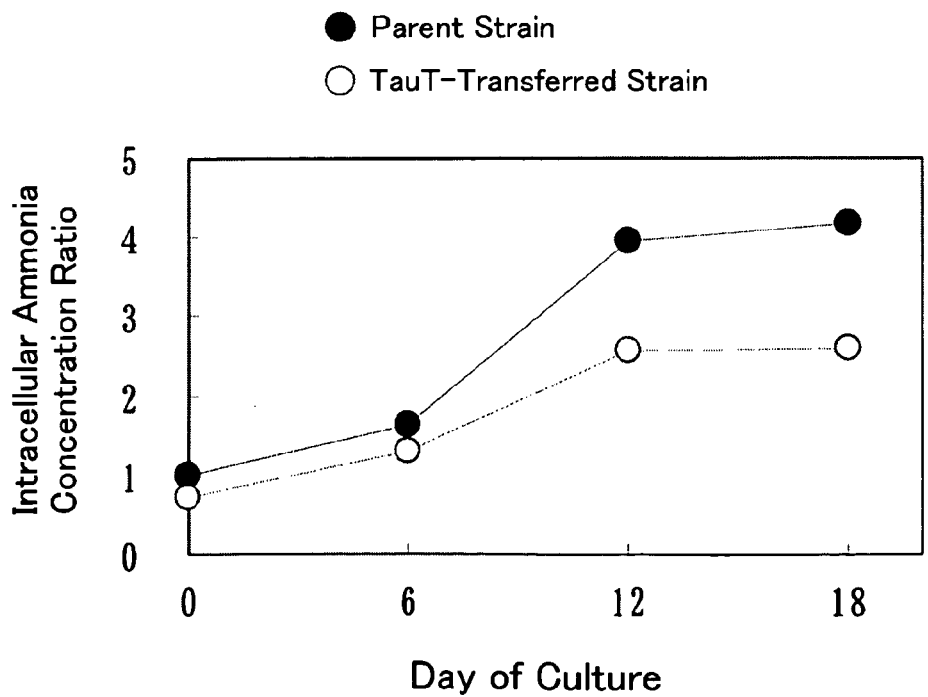
FIG. 11 is a graph showing intracellular ammonia contents (concentration ratios) in 1 L jar fed-batch culture. The ammonia inhibition in pHyg/TauT-transferred strains was remarkable compared to the parent strain.
Figure 12:
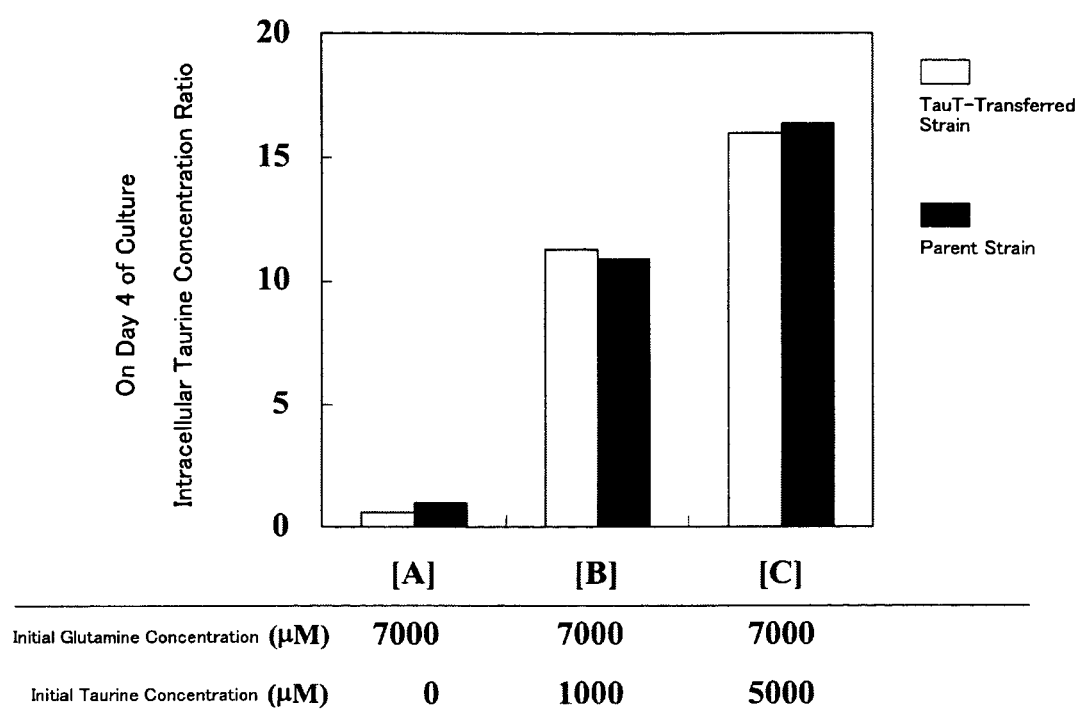
FIG. 12 is a graph showing that taurine is taken into cells depending on the taurine concentration in the medium. No difference was observed in taurine uptake between pHyg/TauT-transferred strains and the parent strain.

As a result, the intracellular ammonia in pHyg/TauT transferred strain was maintained at a low concentration at the late stage of culture; it is believed that this contributes to high antibody yield (FIG. 11).

Intracellular taurine concentration ratios were determined in the same manner as described above for ammonia concentrations (FIG. 12), except that the detected ammonia value per $200 \times 10^5$ cells in the parent strain on day 4 of 50 ml shaker batch culture was taken as 1.

Figure 13:
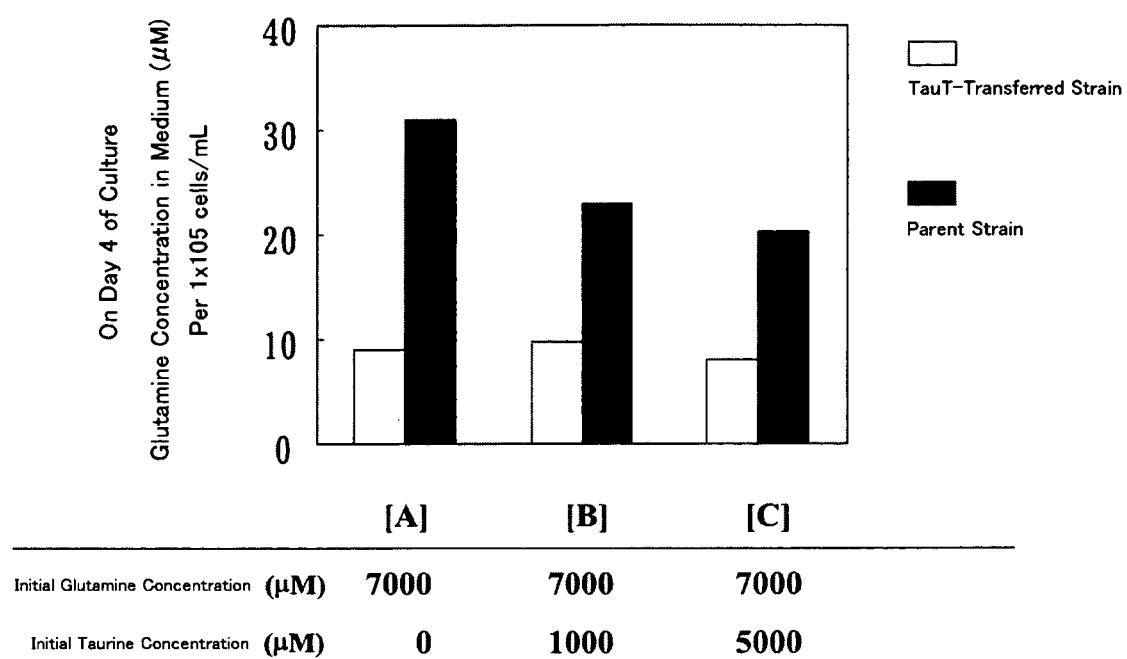
FIG. 13 is a graph showing the consumption of glutamine in the medium. Compared to the parent strain, pHyg/TauT-transferred strains showed a remarkably high glutamine consumption/cell without depending on the taurine concentration in the medium.

As a result, it was found that pHyg/TauT transferred strain had taken up taurine in a manner dependent on the amount of taurine added and that its uptake was almost equal to that by the parent strain. However, as shown in FIG. 13, glutamine consumption in pHyg/TauT transferred strain was remarkably high compared to the parent strain and was not dependent on the initial taurine concentration. It has been reported that glutamine improves cell growth, survival ratio and antibody production ability in hybridomas to thereby raise their antibody yields (Enzyme and Microbial Technology 17:47-55, 1995). Therefore, the antibody production enhancement effect of pHyg/TauT transferred strain may be caused by taurine transporter-mediated uptake of amino acids other than taurine (e.g., glutamine). The glutamine concentrations were obtained by converting the values determined by amino acid analysis of the culture broth on day 4 of culture in FIG. 12 into values per $1 \times 10^5$ cells.

Figure 14:
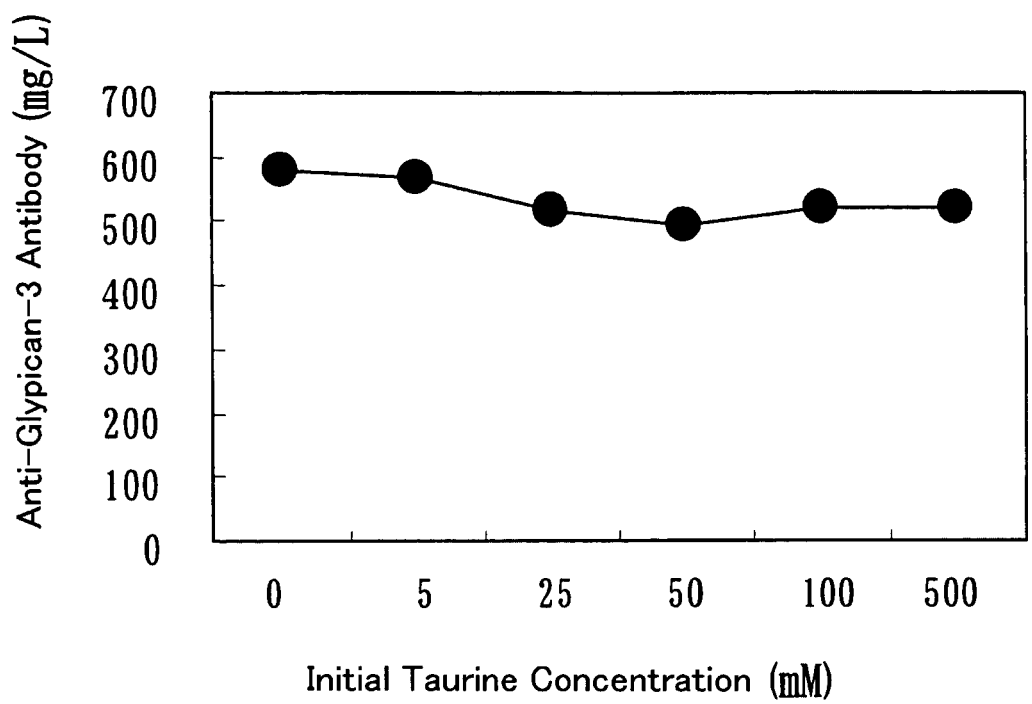
FIG. 14 is a graph showing that the anti-glypican-3 antibody yields of pHyg/TauT-transferred strains are almost equal without depending on the initial taurine concentration in the medium.

Actually, anti-glypican-3 antibody yield was not dependent on the initial taurine concentration (0-500 mM (62.575 g/L)) at the start of 50 ml shaker fed-batch culture (FIG. 14). No significant difference was observed in the parent strains in the effect of initial taurine concentration on antibody yield.

The results described so far suggest that TauT strongly expressing strains have high antibody production ability even if the medium does not contain taurine at the start of culture and that there is a possibility that such strains also promote uptake of amino acids other than taurine.

The present invention is applicable to any antibody-producing cell.

All publications, patent and patent applications cited herein are incorporated herein by reference in their entirety.
Industrial Applicability The present invention is applicable to production of polypeptides.
Sequence Listing free Text
<SEQ ID NO: 1>
SEQ ID NO: 1 shows the nucleotide sequence of a gene encoding hamster taurine transporter.
<SEQ ID NO: 2>
SEQ ID NO: 2 shows the amino acid sequence of hamster taurine transporter.

<SEQ ID NO: 3>
SEQ ID NO: 3 shows the nucleotide sequence of a gene encoding rat taurine transporter.
<SEQ ID NO: 4>
SEQ ID NO: 4 shows the amino acid sequence of rat taurine transporter.
<SEQ ID NO: 5>
SEQ ID NO: 5 shows the nucleotide sequence of a gene encoding mouse taurine transporter.

<SEQ ID NO: 6>
SEQ ID NO: 6 shows the amino acid sequence of mouse taurine transporter.
<SEQ ID NO: 7>
SEQ ID NO: 7 shows the nucleotide sequence of a gene encoding human taurine transporter.
<SEQ ID NO: 8>
SEQ ID NO: 8 shows the amino acid sequence of human taurine transporter.

The invention claimed is:

1. A method of producing a desired secreted polypeptide comprising culturing an isolated mammalian cell transfected with a DNA encoding a taurine transporter and further transfected with a DNA encoding a desired secreted polypeptide, thereby allowing the mammalian cell to produce said desired secreted polypeptide,
wherein the DNA encoding the taurine transporter is any one of the following (a) or (b):
(a) a DNA encoding a polypeptide having the amino acid sequence of SEQ ID NO: 2; or
(b) a DNA encoding a polypeptide having 98% or more amino acid sequence homology with the amino acid sequence of SEQ ID NO: 2, and
wherein the taurine transporter has taurine transporter activity.

2. The method of claim 1, wherein the isolated mammalian cell is a Chinese hamster ovary cell.

3. The method of claim 1, comprising culturing the isolated mammalian cell in a medium with a taurine concentration of 0 to 100 g/L.

4. A method of preparing a pharmaceutical comprising a desired secreted polypeptide, comprising preparing the desired secreted polypeptide by the method of any one of claim 1, 2 or 3 and preparing the pharmaceutical comprising the desired secreted polypeptide.

5. An isolated DNA comprising a DNA encoding a taurine transporter and a heterologous promoter, wherein the DNA encoding the taurine transporter is any one of the following (a) or (b):
(a) a DNA encoding a polypeptide having the amino acid sequence of SEQ ID NO: 2; or
(b) a DNA encoding a polypeptide having 98% or more amino acid sequence homology with the amino acid sequence of SEQ ID NO: 2, and
wherein the taurine transporter has taurine transporter activity.

6. A recombinant vector comprising the isolated DNA of claim 5.

7. An isolated cell transformed or transfected with the isolated DNA of claim 5.

8. The method of claim 1, wherein the desired secreted polypeptide is an antibody.

* * * * *